(12) United States Patent
Maurer et al.

(10) Patent No.: US 8,480,730 B2
(45) Date of Patent: Jul. 9, 2013

(54) SOLID CONSTRUCT MITRAL SPACER

(75) Inventors: Christopher W. Maurer, Wakefield, MA (US); Jonathan E. Wilson, Amesbury, MA (US)

(73) Assignee: Cardiosolutions, Inc., Stoughton, MA (US)

( * ) Notice: Subject to any disclaimer, the term of this patent is extended or adjusted under 35 U.S.C. 154(b) by 1116 days.

(21) Appl. No.: 11/748,138

(22) Filed: May 14, 2007

(65) Prior Publication Data

US 2008/0288061 A1 Nov. 20, 2008

(51) Int. Cl.
*A61F 2/24* (2006.01)

(52) U.S. Cl.
USPC ............................................. 623/2.11

(58) Field of Classification Search
USPC ................ 623/2.11, 2.36, 1.35; 606/153
See application file for complete search history.

(56) References Cited

U.S. PATENT DOCUMENTS

| | | | |
|---|---|---|---|
| 2,549,731 A | 4/1951 | Wattley |
| 2,625,967 A | 1/1953 | Stull |
| 3,197,788 A | 8/1965 | Segger |
| 3,445,916 A | 5/1969 | Schulte |
| 3,551,913 A | 1/1971 | Shiley et al. |
| 3,586,029 A | 6/1971 | Evers et al. |
| 3,589,392 A | 6/1971 | Meyer |
| 3,671,979 A | 6/1972 | Moulopoulos |
| 3,689,942 A | 9/1972 | Rapp |
| 3,714,671 A | 2/1973 | Edwards et al. |
| 3,739,402 A | 6/1973 | Cooley et al. |
| 3,983,581 A | 10/1976 | Angell et al. |
| 4,079,468 A | 3/1978 | Liotta et al. |
| 4,084,268 A | 4/1978 | Ionescu et al. |
| 4,259,753 A | 4/1981 | Liotta et al. |

(Continued)

FOREIGN PATENT DOCUMENTS

| | | |
|---|---|---|
| EP | 1323438 | 2/2003 |
| EP | 0125393 | 8/2007 |

(Continued)

OTHER PUBLICATIONS

Eisenhauer et al., Closure of Prosthetic Paravalvular Mitral Regurgitation With the Gianturco-Grifka Vascular Occlusion Device, Catheterization and Cardiovascular Interventions, 2001, 5 pages,vol. 54.

(Continued)

*Primary Examiner* — Corrine M McDermott
*Assistant Examiner* — Christina Lauer
(74) *Attorney, Agent, or Firm* — Grossman Tucker Perreault & Pfleger PLLC

(57) ABSTRACT

A heart valve implant according to one embodiment may include a shaft extending generally along a longitudinal axis of the heart valve implant having at least one anchor configured to be coupled to a first end of the shaft. A spacer may include a plurality of individual segments each including at least one passageway configured to be disposed about the shaft. The plurality of individual segments may define an outer surface of the spacer which is configured to interact with at least a portion of at least one cusp of a heart valve to at least partially restrict a flow of blood through the heart valve in a closed position. The plurality of individual segments may each having a length and at least one cross-section dimension no larger than an internal cross-section of a lumen of a delivery catheter.

12 Claims, 7 Drawing Sheets

U.S. PATENT DOCUMENTS

| | | | |
|---|---|---|---|
| 4,291,420 A | 9/1981 | Reul | |
| 4,297,749 A | 11/1981 | Davis et al. | |
| 4,439,185 A | 3/1984 | Lundquist | |
| 4,535,757 A | 8/1985 | Webster, Jr. | |
| 4,597,767 A | 7/1986 | Lenkei | |
| 4,865,030 A | 9/1989 | Polyak | |
| 4,960,424 A | 10/1990 | Grooters | |
| 5,002,067 A | 3/1991 | Berthelsen et al. | |
| 5,217,484 A | 6/1993 | Marks | |
| 5,222,973 A | 6/1993 | Sharpe et al. | |
| 5,261,916 A | 11/1993 | Engelson | |
| 5,304,195 A | 4/1994 | Twyford, Jr. et al. | |
| 5,308,357 A | 5/1994 | Lichtman | |
| 5,318,589 A | 6/1994 | Lichtman | |
| 5,350,397 A | 9/1994 | Palermo et al. | |
| 5,397,351 A | 3/1995 | Pavcnik et al. | |
| 5,415,667 A | 5/1995 | Frater | |
| 5,462,527 A | 10/1995 | Stevens-Wright et al. | |
| 5,509,428 A | 4/1996 | Dunlop | |
| 5,582,607 A | 12/1996 | Lackman | |
| 5,611,800 A | 3/1997 | Davis et al. | |
| 5,634,936 A | 6/1997 | Linden et al. | |
| 5,638,827 A | 6/1997 | Palmer et al. | |
| 5,649,949 A | 7/1997 | Wallace et al. | |
| 5,653,712 A | 8/1997 | Stern | |
| 5,665,100 A | 9/1997 | Yoon | |
| 5,776,075 A | 7/1998 | Palmer | |
| 5,792,179 A | 8/1998 | Sideris | |
| 5,797,958 A | 8/1998 | Yoon | |
| 5,814,098 A | 9/1998 | Hinnenkamp et al. | |
| 5,891,130 A | 4/1999 | Palermo et al. | |
| 5,895,391 A | 4/1999 | Farnholtz | |
| 5,928,224 A | 7/1999 | Laufer | |
| 5,957,865 A | 9/1999 | Backman et al. | |
| 5,957,949 A | 9/1999 | Leonhardt et al. | |
| 5,989,242 A | 11/1999 | Saadat et al. | |
| 5,993,474 A | 11/1999 | Ouchi | |
| 6,090,096 A | 7/2000 | St. Goar et al. | |
| 6,152,144 A * | 11/2000 | Lesh et al. | 128/898 |
| 6,190,373 B1 | 2/2001 | Palermo et al. | |
| 6,217,610 B1 | 4/2001 | Carpentier et al. | |
| 6,283,995 B1 | 9/2001 | Moe et al. | |
| 6,287,339 B1 | 9/2001 | Vazquez et al. | |
| 6,332,893 B1 | 12/2001 | Mortier et al. | |
| 6,358,277 B1 | 3/2002 | Duran | |
| 6,415,693 B1 | 7/2002 | Simon et al. | |
| 6,419,695 B1 | 7/2002 | Gabbay | |
| 6,440,132 B1 | 8/2002 | Jackson | |
| 6,454,798 B1 | 9/2002 | Moe | |
| 6,461,382 B1 | 10/2002 | Cao | |
| 6,482,228 B1 | 11/2002 | Norred | |
| 6,508,825 B1 | 1/2003 | Selmon et al. | |
| 6,592,606 B2 | 7/2003 | Huter et al. | |
| 6,652,578 B2 | 11/2003 | Bailey et al. | |
| 6,673,100 B2 | 1/2004 | Diaz et al. | |
| 6,746,404 B2 | 6/2004 | Schwartz | |
| 6,764,510 B2 | 7/2004 | Vidlund et al. | |
| 6,769,434 B2 | 8/2004 | Liddicoat et al. | |
| 6,821,297 B2 | 11/2004 | Snyders | |
| 6,849,081 B2 | 2/2005 | Sepetka et al. | |
| 6,869,444 B2 | 3/2005 | Gabbay | |
| 6,896,700 B2 | 5/2005 | Lu et al. | |
| 6,911,043 B2 | 6/2005 | Myers et al. | |
| 6,971,998 B2 | 12/2005 | Rosenman et al. | |
| 6,974,476 B2 | 12/2005 | McGuckin, Jr. et al. | |
| 7,018,406 B2 | 3/2006 | Seguin et al. | |
| 7,056,286 B2 | 6/2006 | Ravenscroft et al. | |
| 7,070,618 B2 | 7/2006 | Streeter | |
| 7,077,862 B2 | 7/2006 | Vidlund et al. | |
| 7,101,395 B2 | 9/2006 | Tremulis et al. | |
| 7,112,219 B2 | 9/2006 | Vidlund et al. | |
| 7,160,322 B2 | 1/2007 | Gabbay | |
| 7,189,199 B2 | 3/2007 | McCarthy et al. | |
| 7,247,134 B2 | 7/2007 | Vidlund et al. | |
| 7,344,553 B2 | 3/2008 | Opolski et al. | |
| 7,374,572 B2 | 5/2008 | Gabbay | |
| 7,381,210 B2 | 6/2008 | Zarbatany et al. | |
| 7,404,824 B1 | 7/2008 | Webler et al. | |
| 7,657,326 B2 | 2/2010 | Bodner et al. | |
| 7,678,145 B2 | 3/2010 | Vidlund et al. | |
| 7,753,949 B2 | 7/2010 | Lamphere et al. | |
| 7,785,366 B2 | 8/2010 | Maurer et al. | |
| 8,092,525 B2 | 1/2012 | Eliasen et al. | |
| 8,216,302 B2 | 7/2012 | Wilson et al. | |
| 2002/0042651 A1 | 4/2002 | Liddicoat et al. | |
| 2002/0058995 A1* | 5/2002 | Stevens | 623/2.11 |
| 2002/0077566 A1 | 6/2002 | Laroya et al. | |
| 2002/0081553 A1 | 6/2002 | Tramonte | |
| 2002/0183838 A1 | 12/2002 | Liddicoat et al. | |
| 2002/0188170 A1 | 12/2002 | Santamore et al. | |
| 2003/0033009 A1 | 2/2003 | Gabbay | |
| 2003/0040792 A1 | 2/2003 | Gabbay | |
| 2003/0105519 A1 | 6/2003 | Fasol et al. | |
| 2003/0130731 A1 | 7/2003 | Vidlund et al. | |
| 2003/0139751 A1 | 7/2003 | Evans et al. | |
| 2003/0144574 A1 | 7/2003 | Heilman et al. | |
| 2003/0181945 A1 | 9/2003 | Opolski et al. | |
| 2003/0199975 A1 | 10/2003 | Gabbay | |
| 2003/0208203 A1 | 11/2003 | Lim et al. | |
| 2003/0212453 A1 | 11/2003 | Mathis et al. | |
| 2004/0034366 A1 | 2/2004 | van der Burg et al. | |
| 2004/0044402 A1 | 3/2004 | Jung et al. | |
| 2004/0088047 A1 | 5/2004 | Spence et al. | |
| 2004/0106989 A1 | 6/2004 | Wilson et al. | |
| 2004/0122512 A1 | 6/2004 | Navia et al. | |
| 2004/0127981 A1 | 7/2004 | Rahdert et al. | |
| 2004/0127983 A1 | 7/2004 | Mortier et al. | |
| 2004/0148020 A1 | 7/2004 | Vidlund et al. | |
| 2004/0181256 A1 | 9/2004 | Glaser | |
| 2004/0210304 A1 | 10/2004 | Seguin et al. | |
| 2004/0210307 A1 | 10/2004 | Khairkhahan | |
| 2004/0225353 A1 | 11/2004 | McGuckin, Jr. et al. | |
| 2004/0225354 A1 | 11/2004 | Allen et al. | |
| 2004/0243229 A1 | 12/2004 | Vidlund et al. | |
| 2005/0021056 A1 | 1/2005 | Goar et al. | |
| 2005/0033446 A1 | 2/2005 | Deem et al. | |
| 2005/0038508 A1 | 2/2005 | Gabbay | |
| 2005/0038509 A1 | 2/2005 | Ashe | |
| 2005/0065591 A1 | 3/2005 | Moberg et al. | |
| 2005/0070999 A1 | 3/2005 | Spence | |
| 2005/0075727 A1 | 4/2005 | Wheatley | |
| 2005/0090824 A1 | 4/2005 | Shluzas et al. | |
| 2005/0131451 A1 | 6/2005 | Kleshinski et al. | |
| 2005/0159810 A1 | 7/2005 | Filsoufi | |
| 2005/0222488 A1 | 10/2005 | Chang et al. | |
| 2005/0288786 A1* | 12/2005 | Chanduszko | 623/11.11 |
| 2006/0025855 A1 | 2/2006 | Lashinski et al. | |
| 2006/0058871 A1 | 3/2006 | Zakay et al. | |
| 2006/0084943 A1 | 4/2006 | Rosenman et al. | |
| 2006/0129025 A1 | 6/2006 | Levine et al. | |
| 2006/0149368 A1 | 7/2006 | Spence | |
| 2006/0155326 A1 | 7/2006 | Aranyi | |
| 2006/0178700 A1 | 8/2006 | Quinn | |
| 2006/0195012 A1 | 8/2006 | Mortier et al. | |
| 2006/0195185 A1 | 8/2006 | Lane et al. | |
| 2006/0199995 A1 | 9/2006 | Vijay | |
| 2006/0229708 A1 | 10/2006 | Powell et al. | |
| 2006/0241745 A1 | 10/2006 | Solem | |
| 2006/0253072 A1 | 11/2006 | Pai et al. | |
| 2006/0293698 A1 | 12/2006 | Douk | |
| 2007/0049980 A1 | 3/2007 | Zielinski et al. | |
| 2007/0093890 A1 | 4/2007 | Eliasen et al. | |
| 2007/0118151 A1 | 5/2007 | Davidson | |
| 2007/0167981 A1 | 7/2007 | Opolski et al. | |
| 2007/0185571 A1 | 8/2007 | Kapadia et al. | |
| 2007/0198050 A1 | 8/2007 | Ravenscroft et al. | |
| 2007/0198082 A1 | 8/2007 | Kapadia et al. | |
| 2007/0213578 A1 | 9/2007 | Khairkhahan et al. | |
| 2007/0232981 A1 | 10/2007 | Ravenscroft et al. | |
| 2007/0239154 A1 | 10/2007 | Shaolian et al. | |
| 2007/0255399 A1 | 11/2007 | Eliasen et al. | |
| 2007/0265700 A1 | 11/2007 | Eliasen et al. | |
| 2007/0282429 A1 | 12/2007 | Hauser et al. | |
| 2007/0293943 A1 | 12/2007 | Quinn | |
| 2008/0125860 A1 | 5/2008 | Webler et al. | |
| 2008/0125861 A1 | 5/2008 | Webler et al. | |
| 2008/0183105 A1 | 7/2008 | Greenhalgh et al. | |

| | | | |
|---|---|---|---|
| 2008/0195200 | A1 | 8/2008 | Vidlund et al. |
| 2009/0043382 | A1 | 2/2009 | Maurer et al. |
| 2009/0048668 | A1 | 2/2009 | Wilson et al. |
| 2009/0105814 | A1 | 4/2009 | Groothuis et al. |
| 2009/0131849 | A1 | 5/2009 | Maurer et al. |
| 2009/0131880 | A1 | 5/2009 | Speziali et al. |
| 2009/0132033 | A1 | 5/2009 | Maurer et al. |
| 2009/0163934 | A1 | 6/2009 | Raschdorf, Jr. et al. |
| 2009/0240326 | A1 | 9/2009 | Wilson et al. |
| 2010/0022948 | A1 | 1/2010 | Wilson et al. |
| 2010/0324668 | A1 | 12/2010 | Maurer et al. |
| 2012/0143320 | A1 | 6/2012 | Eliasen et al. |

FOREIGN PATENT DOCUMENTS

| | | |
|---|---|---|
| GB | 1264472 | 2/1972 |
| GB | 1268484 | 3/1972 |
| GB | 1388064 | 3/1975 |
| WO | 03/049619 | 6/2003 |
| WO | 2006032051 | 3/2006 |
| WO | 2006/064490 A1 | 6/2006 |
| WO | 2006091597 | 8/2006 |
| WO | 2006/111391 | 10/2006 |
| WO | 2006127509 | 11/2006 |
| WO | 2007064810 | 6/2007 |
| WO | 2007078772 | 7/2007 |
| WO | 2007100409 | 9/2007 |
| WO | 2007/140470 A2 | 12/2007 |
| WO | 2008079828 | 7/2008 |
| WO | 2009053952 A2 | 4/2009 |

OTHER PUBLICATIONS

Hourihan et al., Transcatheter Umbrella Closure of Valvular and Paravalvular Leaks, American College of Cardiology, Nov. 15, 1992, 7 pages, vol. 20, No. 6.
Moscucci et al., Coil Embolization of a Periprosthetic Mitral Valve Leak Associated With Severe Hemolytic Anemia, Images in Cardiovascular Medicine, American Heart Association, Inc., 2001, 2 pages, vol. 104.
Rashkind et al. Nonsurgical closure of patent ductus arteriosus: clinical application of the Rashkind PDA Occluder System, Therapy and Prevention—Congenital Heart Disease, Mar. 1987, 10 pages, vol. 75, No. 3.
Ryhänen et al., Invivo biocompatibility evaluation of nickel-titanium shape memory metal alloy: Muscle and perineural tissue responses and encapsule membrane thickness, Muscle and Perineural Tissue Response to Nitinol, accepted Jan. 19, 1998, 8 pages.
International Search Report and Written Opinion dated Jan. 16, 2009 issued in PCT Application No. PCT/US08/83497, 10 pages.
Balzer et al., Real-time transesophageal three-dimensional echocardiography for guidance of percutaneous cardiac interventions: first experience, Clinical Research in Cardiology, May 29, 2008, 565-574, vol. 97, No. 9.
Carlson et al., Lead Perforation: Incidence in Registries, Pace Industry Viewpoint, Jan. 2008, 13-15, vol. 31.
Clinical Trials.gov, Comparing the Effectiveness of a Mitral Valve Repair Procedure in Combination With Coronary Artery Bypass Grafting (CABG) Versus CABG Alone in People with Moderate Ischemic Mitral Regurgitation, http://clinicaltrials.gov/ct2/show/record/NCT00806988?term=mitral+repair&rank=7, Feb. 24, 2009, 1-3.
Clinical Trials.gov, Safety and Efficacy Study of the PTMA Device to Reduce Mitral Valve Regurgitation in Patients With Heart Failure (PTOLEMY2Canada), http://clinicaltrials.gov/ct2/show/study/NCT00815386?term=Viacor&rank=3, 1-3.
Clinical Trials.gov, Study of Safety and Efficacy of the Percutaneous Reduction of Mitral Valve Regurgitation in Heart Failure Patients (PTOLEMY-2), http://clinicaltrials.gov/ct2/show/NCT00787293?term=Viacor&rank=5, 1-2.
Cohen, Trans-Septal Technique for Tandemheart Insertion, Lenox Hill Heart and Vascular Institute of New York, Barcelona May 22-May 25, 2007, 18 pages.
Corbisiero et al., Does Size Really Matter? A Comparison of the Riata Lead Family Based on Size and Its Relation to Performance, Pace, Jun. 2008, vol. 31, 722-726.

Criber et al., Treatment of Calcific Aortic Stenosis With the Percutaneous Heart Valve—Mid-Term Follow-Up From the Initial Feasibility Studies: The French Experience, Journal of the American College of Cardiology, Mar. 21, 2006, vol. 47, No. 6, 1241-1223.
Danik et al., Timing of delayed perforation with the St. Jude Riata lead: A single-center experience and a review of the literature, Heart Rhythm Society, Dec. 2008, vol. 5, No. 12, 1667-1672.
Del Valle-Fernández et al., Transcatheter heart valves for the treatment of aortic stenosis: state-of-the-art, Minerva Cardioangiologica, Oct. 2008, vol. 56, No. 5, 543-556.
Douthitt, Cardiac Dimensions® Inc. Receives CE Mark for CARILLON™ Mitral Contour System™, Cardiac Dimensions—News, htpp://www.cardiacdimensions.com/usa/press-release-2-4-09.html, downloaded Feb. 24, 2009, 1-2.
Dvorin, Endovalve Inc., Pioneering percutaneous mitral valve replacement., Start-Up Windhover's Review of Emerging Medical Ventures, Jun./Jul. 2006, vol. 11, No. 7, 1-2.
Eltchaninoff, Clinical results of percutaneous aortic valve implantation, Euro PCR07, Cribier-Edwards, 30 pages.
Evalve reports 1st MitraClip treatments in the Netherlands, Medical Device Daily, Feb. 19, 2009, vol. 13, No. 32, 2 pages.
A first for MiCardia's Dynoplasty, Medical Device Daily, Feb. 19, 2009, vol. 13, No. 32, 1 page.
Fitts et al. , Fluoroscopy-Guided Femoral Artery Puncture Reduces the Risk of PCI-Related Vascular Complications, Journal of Interventional Cardiology, vol. 21, No. 3, 2008, 273-278.
Gelsomino et al., Left ventricular diastolic function after restrictive mitral ring annuloplasty in chronic ischemic mitral regurgitation and its predictive value on outcome and recurrence of regurgitation, International Journal of Cardiology, vol. 132, 2009, 419-428.
Geyfman et al., Cardiac Tamponade as Complication of Active-Fixation Atrial Lead Perforations: Proposed Mechanism and Management Algorithm, PACE, Apr. 2007, vol. 30, 498-501.
Gorman et al., Surgical Therapy for Mitral Regurgitation: The Key to Preventing Heart Failure?, Prevention of Heart Failure After Myocardial Infarction, 2008, 211-215.
Harper, Evalve Announces Enrollment Completion of the Everest Randomized Study, http://www.evalveinc.com/europe/press/17.html, downloaded Feb. 24, 2009, 1-3.
Harper, Two-Year Follow-Up Data Demonstrates Preservation of Adequate Mitral Valve Area in Patients Treated with the MitraClip®-system, http://www.evalveinc.com/europe/press/21.html, downloaded Feb. 24, 2009, 1-3.
Hung et al., 3D Echocardiography: A Review of the Current Status and Future Directions, ASE Position Paper, Journal of the American Society of Echocardiography, Mar. 2007, 213-233.
Hung et al., Mechanism of Dynamic Regurgitant Orifice Area Variation of Functional Mitral Regurgitation—Physiologic Insights From the Proximal Flow Convergence Technique, Journal of the American College of Cardiology, Feb. 1999, vol. 33, No. 2, 538-545.
Hung et al., A Novel Approach for Reducing Ischemic Mitral Regurgitation by Injection of a Polymer of Reverse Remodel and Reposition Displaced Papillary Muscles, Circulation—Journal of the American Heart Association, Sep. 30, 2008, Downloaded from circ.ahajournals.org at National Insthealth Lib on Feb. 25, 2009, S262-S269.
Hytowitz, First U.S. Patients Enrolled in the Realism Continued Access Study, evalve, http://www.evalveinc.com/europe/press/22/html, downloaded Feb. 24, 2009, 2 pages.
International Search Report and Written Opinion dated Feb. 25, 2009 issued in PCT Application No. PCT/US08/83570, 13 pages.
International Search Report and Written Opinion dated Apr. 2, 2009 issued in PCT Application No. PCT/US08/83574, 8 pages.
Jilaihawi et al., Percutaneous Aortic Valve Replacement in Patients with Challenging Aortoiliofemoral Access, Catheterization and Cardiovascular Interventions, 2008, vol. 72, 885-890.
Jovin et al., Atrial Fibrillation and Mitral Valve Repair, Pace, Aug. 2008, vol. 31, 1057-1063.
Kahlert et al., Direct Assessment of Size and Shape of Noncircular Vena Contracta Area in Functional Versus Organic Mitral Regurgitation Using Real-Time Three-Dimensional Echocardiography, Valvular Heart Disease, Journal of the American Society of Echocardiography, Aug. 2008, vol. 21, No. 8, 912-921.

Kempfert et al., Minimally invasive off-pump valve-in-a-valve implantation: the atrial transcatheter approach for re-operative mitral valve replacement, European Heart Journal, 2008, vol. 29, 2382-2387.

Kerensky, Complications of Cardiac Catheterization and Strategies to Reduce Risks, Diagnostic and Therapeutic Cardiac Catheterization—Third Edition—Chapter 8, 1998, 17 pages.

Kodali et al., Transcatheter Valve Repair and Replacement, Downloaded from arjournals.annualreviews.org by National Institute of Health Library on Feb. 25, 2009, 14 pages.

Kwan et al., Geometric Differences of the Mitral Apparatus Between Ischemic and Dilated Cardiomyopathy With Significant Mitral Regurgitation—Real-Time Three-Dimensional Echocardiography Study, Circulation, Mar. 4, 2003, 1135-1140.

Leung et al., Percutaneous Mitral Valve Repair—An overview of the current devices and techniques, Coronory/Cardiac Interventions—Endovascular Today, Oct. 2006, 26-33.

Levine et al., Mechanistic Insights into Functional Mitral Regurgitation, Valvular Heart Disease, 2009, 125-129.

Little et al., Three-Dimensional Ultrasound Imaging Model of Mitral Valve Regurgitation: Design and Evaluation, Ultrasound in Medicine and Biology, 2008, vol. 34, No. 4, 647-654.

Llaneras et al., Large Animal Model of Ischemic Mitral Regurgitation, The Society of Thoracic Surgeons—Ischemic Mitral Insufficiency, 1994, vol. 57, 432-439.

Magne et al., Ischemic Mitral Regurgitation: A Complex Multifaceted Disease, Cardiology, 2009, vol. 112, 244-259.

McClure et al., Early and late outcomes in minimally invasive mitral valve repair: An eleven-year experience in 707 patients, Acquired Cardiovascular Disease, The Journal of Thoracic and Cardiovascular Surgery, Jan. 2009, vol. 137, No. 1, 70-75.

Modi et al., Minimally invasive mitral valve surgery: a systematic review and meta-analysis, European Journal of Cardio-Thoracic Surgery, 2008, vol. 34, 943-952.

Myers, Jr., et al., Color Doppler Velocity Accuracy Proximal to Regurgitant Orifices: Influence of Orifice Aspect Ratio, Ultrasound in Medicine and Biology, 1999, vol. 25, No. 5, 771-792.

Ning et al., Live three-dimensional transesophageal echocardiography in mitral valve surgery, Chinese Medical Journal, 2008, vol. 121, No. 20, 2037-2041.

Nötzold et al., Microemboli in aortic valve replacement, Future Drugs Ltd, Expert Rev. Cardiovasc. Ther., vol. 4, No. 6, 2006, 853-859.

Onundarson et al., Warfarin anticoagulation intensity in specialist-based and in computer-assisted dosing practice, International Journal of Laboratory Hematology, 2008, vol. 30, 382-389.

Otsuji et al., Insights From Three-Dimensional Echocardiography Into the Mechanism of Functional Mitral Regurgitation—Direct In Vivo Demonstration of Altered Leaflet Tethering Geometry, Circulation, Sep. 16, 1997, vol. 96, No. 6, 1999-2008.

Fukuda et al., Maintenance of Geometric Alterations Associated with Percutaneous Mitral Valve Repair: Real-Time Three-Dimensional Echocardiographic Assessment in an Ovine Model, J. Heart Valve Dis, May 2008, vol. 17, No. 3, 276-282.

Pai et al., Effect of Atrial Fibrillation on the Dynamics of Mitral Annular Area, J. Heart Valve Dis., Jan. 2003, vol. 12, No. 1, 31-37.

Palacios et al., Safety and Feasibility of Acute Percutaneous Septal Sinus Shortening: First-In-Human Experience, Catheterization and Cardiovascular Interventions, 2007, vol. 69, 513-518.

Paniagua et al., First Human Case of Retrograde Transcatheter Implantation of an Aortic Valve Prosthesis, Texas Heart Institute Journal, Transcatheter Aortic Valve Prosthesis, 2005, vol. 32, No. 3, 393-398.

Rodés-Cabau et al., Feasibility and Initial Results of Percutaneous Aortic Valve Implantation Including Selection of the Transfemoral or Transapical Approach in Patients With Severe Aortic Stenosis, The American Journal of Cardiology, 2008, 1240-1246.

Satpathy et al., Delayed Defibrillator Lead Perforation: An Increasing Phenomenon, Pace, Jan. 2008, vol. 31, 10-12.

Schofer, Percutaneous MVR: Clinical Evaluation—The Carillon Experience, EuroPCR 2007, Barcelona, Spain, May 22-25, 2007, 35 pages.

Schwammenthal et al., Dynamics of Mitral Regurgitant Flow and Orifice Area—Physiologic Application of the Proximal Flow Convergence Method: Clinical Data and Experimental Testing, Circulation, Jul. 1994, vol. 90, No. 1, 307-322.

Spencer, Viacor, Inc. Announces First Patient Treated in PTOLEMY-2 Study, http://www.viacorinc.com/viacor_news.html, Nov. 14, 2008, downloaded Feb. 24, 2009, 2 pages.

Sterliński et al., Subacute cardiac perforations associated with active fixation leads, Clinical Research Leads and Lead Extraction, Europace, 2009, vol. 11, 206-212.

Turakhia et al., Rates and severity of perforation from implantable cardioverter-defibrillator leads: A 4-year study, J Interv Card Electrophysiol, 2009, vol. 24, 47-52.

Vahanian, The Cardiologist's Perspective on the Future of Percutaneous Mitral Valve Repair, Euro PCR07, 53 pages.

Vahanian, Coronary Sinus and Direct Annuloplasty Percutaneous Mitral Valve Repair, Innovations in Cardiovascular Interventions, Dec. 7-9, 2008, Tel-Aviv, Israel, 45 pages.

Vahanian, Edwards MONARC system—Evolution Interim Results, 31 pages.

Vahanian, Overview on Percutaneous Mitral Valve Technology, Euro PCR07, Transcatheter Valve Symposium, Barcelona, May 22-25, 2007, 29 pages.

Van Gelder et al., Diagnosis and Management of Inadvertently Placed Pacing and ICD Leads in the Left Ventricle: A Multicenter Experience and Review of the Literature, Pace, May 2000, vol. 23, 877-883.

Vranckx et al., The TandemHeart®, percutaneous transseptal left ventricular assist device: a safeguard in high-risk percutaneous coronary interventions. The six-year Rotterdam experience, Clinical research EuroInterv., 2008, vol. 4, 331-337.

Wolf et al., Solid and gaseous cerebral micoembolization after biologic and mechanical aortic valve replacement: Investigation with multirange and multifrequency transcranial Doppler ultrasound, The Journal of Thoracic and Cardiovascular Surgery, Mar. 2008, vol. 135, No. 3, 512-520.

Xiangming et al., In Vivo Characterization of Attachment Safety Between Cardiac Pacing Lead and Canine Heart Muscle*, Acta Mechanica Solida Sinica, Sep. 2007, vol. 20, No. 3, 189-197.

Yamaura et al., Geometrical Demonstration and Three-Dimensional Quantitative Analysis of the Mitral Valve With Real-Time Three-Dimensional Echocardiography: Novel Anatomical Image Creation System, J Echocardiogr, 2004, vol. 2, No. 4, 99-104.

Yosefy et al., Proximal Flow Convergence Region as Assessed by Real-time 3-Dimensional Echocardiography: Challenging the Hemispheric Assumption, Journal of the American Society of Echocardiography, Apr. 2007, vol., No. 4, 389-396.

Matthews, Anatomy of the Heart, Definitions Cardiology Explained and Presented by Robert Matthews, MD, http://www.rjmatthewsmd.com/Definitions/anatomy_ofthe_heart.htm, printed Jul. 28, 2008, 265 pages.

Mullens, Vascular access, Cardiac Catheterization in Congenital Heart Disease; Pediatric and Adult, 2006, Chapter 4, pp. 115-117, 5 pages, Blackwell Futura, USA.

Mullens, Aortic valve dilation, Cardiac Catheterization in Congenital Heart Disease; Pediatric and Adult, 2006, Chapter 19, pp. 487-489, 5 pages, Blackwell Futura, USA.

Mullens, Foreign body removal, Cardiac Catheterization in Congenital Heart Disease; Pediatric and Adult, 2006, Chapter 12, pp. 350-377, 30 pages, Blackwell Futura, USA.

Mullens, Flow directed catheters ("floating" balloon catheters), Cardiac Catheterization in Congenital Heart Disease; Pediatric and Adult, 2006, Chapter 7, pp. 213-221, 9 pages, Blackwell Futura, USA.

International Search Report and Written Opinion, May 11, 2007 (6 pages).

Trippel, et al., "Reinforced Ivalon Sponge as an Aortic Prosthesis" Feb. 1960 (9 pages).

Johns, et al., "Mitral Insufficiency: the Experimental Use of a Mobile Polyvinyl Sponge Prosthesis" Sep. 1954 (pp. 335-341).

Glenn, et al., "The Surgical Treatment of Mitral Insufficiency: the Fate of a Vascularized Transchamber Intracardiac Graft" Apr. 1955 (pp. 510-518).

Carter, et al. "Surgical Treatment of Mitral Insufficiency" 1953 (pp. 574-583).
Harken, et al., "The Surgical Treatment of Mitral Insufficiency" 1954 (pp. 604-627).
Benichoux, et al., "A Method of Surgical Correction of Mitral Insufficiency" 1955 (pp. 148-158).
Glenn, et al., "The Surgical Treatment of Mitral Insufficiency with Particular Reference to the Application of a Vertically Suspended Graft" Jul. 1956 (pp. 59-77).
Harken, et al., "The Surgical Correction of Mitral Insufficiency" 1953 (pp. 4-7).
Sakakibara, "A Surgical Approach to the Correction of Mitral Insufficiency" Aug. 1955 (pp. 196-203).
Bailey, et al., "Surgical Repair of Mitral Insufficiency" Feb. 1951 (pp. 125-182).
Bailey, et al., "Closed Intracardiac Tactile Surgery" Jul. 1952 (pp. 1-24).
Blalock, "A Consideration of Some of the Problems in Cardiovascular Surgery" Jun. 1951 (pp. 543-571).
Bailey, et al., "The Surgical Correction of Mitral Insufficiency by the Use of Pericardial Grafts" Dec. 1954 (pp. 551-627).
Borrie, "Mitral Insufficiency: Experimental Circular Suture Around the Atrioventricular Ring" 1955 (pp. 687-697).
Moore, et al., "Unsuitability of Transventricular Autogenous Slings for Diminishing Valvular Insufficiency" Feb. 1953 (pp. 173-182).
Henderson, et al., "The Surgical Treatment of Mitral Insufficiency" Jun. 1953 (pp. 858-868).
Glover, et al., "The Fate of Intracardiac Pericardial Grafts as Applied to the Closure of Septal Defects and to the Relief of Mitral Insufficiency" 1952 (pp. 178-185).
Glenn, et al., "The Implantation of a Vascularized Graft in the Chambers of the Heart" 1954 (pp. 5-11).
Acar et al., AREVA: Multicenter Randomized Comparison of Low-Dose Versus Standard-Dose Anticoagulation in Patients With Mechanical Prosthetic Heart Valves, Circulation, Nov. 1, 1996, 2107-12, vol. 94, No. 9.
Acker et al., Mitral valve surgery in heart failure: Insights from the Acorn Clinical Trial, Surgery for Acquired Cardiovascular Disease, The Journal of Thoracic and Cardiovascular Surgery, Sep. 2006, 568-577.e4, vol. 132, No. 3.
Babaliaros et al., Emerging Applications for Transseptal Left Heart Catheterization—Old Techniques for New Procedures, Journal of the American College of Cardiology, Jun. 3, 2008, 2116-22, vol. 51, No. 22.
Kuck et al., Best of Structural Heart Disease Abstracts, TCT-124, The American Journal of Cardiology, Oct. 20-25, 2007, 58L.
Rinaldi et al., Best of Structural Heart Disease Abstracts, TCT-123, The American Journal of Cardiology, Oct. 20-25, 2007, 57L.
Siminiak et al., Best of Structural Heart Disease Abstracts, TCT-125, The American Journal of Cardiology, Oct. 20-25, 2007, 58L.
B-Lundqvist et al., Transseptal Left Heart Catheterization: A Review of 278 Studies, Clin. Cardiol., Jan. 1986, 21-26, vol. 9.
Bonow et al., ACC/AHA 2006 Guidelines for the Management of Patients With Valvular Heart Disease: Executive Summary, Circulation—Journal of the American Heart Association, Downloaded from circ.ahajournals.org, Jul. 31, 2008, 449-527.
Braunberger et al., Very Long-Term Results (More Than 20 Years) of Valve Repair With Carpentier's Techniques in Nonrheumatic Mitral Valve Insufficiency, Downloaded from circ.ahajournals.org, Aug. 26, 2008, I-8-I-11.
Bryan et al., Prospective randomized comparison of CarboMedics and St. Jude Medical bileaflet mechanical heart valve prostheses: Ten-year follow-up, The Journal of Thoracic and Cardiovascular Surgery, Mar. 2007, 614-622.e2, vol. 133, No. 3.
Burkhoff et al., A randomized multicenter clinical study to evaluate the safety and efficacy of the Tandem Heart percutaneous ventricular assist device versus conventional therapy with intraaortic balloon pumping for treatment of cardiogenic shock, American Heart Journal, Sep. 2006, 469.e1-469.e8, vol. 152, No. 3.
Byrne et al., Percutaneous Mitral Annular Reduction Provides Continued Benefit in an Ovine Model of Dilated Cardiomyopathy, Downloaded from circ.ahajournals.org, Aug. 26, 2008, 3088-92.
Carpentier et al., Reconstructive surgery of mitral valve incompetence Ten-year appraisal, The Journal of Thoracic and Cardiovascular Surgery, Mar. 1980, 338-348, vol. 79, No. 3.
Casselman et al., Mitral Valve Surgery Can Now Routinely Be Performed Endoscopically, Downloaded from circ.ahajournals.org, Aug. 26, 2008, II-48-II-54.
Cauchemez et al., High-Flow Perfusion of Sheaths for Prevention of Thromboembolic Complications During Complex Catheter Ablation in the Left Atrium, Journal of Cardiovascular Electrophysiology, Mar. 2004, 276-283, vol. 15, No. 3.
ClinicalTrials.gov, Aachen Safety and Efficacy of the Percutaneous Transvenous Mitral Annuloplasty Device to Reduce Mitral Regurgitation (PTOLEMY), http://clinicaltrials.gov/ct2/show/NCT00572091?term=mitral+regurgitation&rank=2, Aug. 25, 2008, 1-3.
ClinicalTrials.gov, Feasibility Study of a Percutaneous Mitral Valve Repair System., http://clinicaltrials.gov/ct2/show/NCT00209339?term=mitral+valve&rank=3, Aug. 25, 2008, 1-4.
ClinicalTrials.gov, Montreal Safety and Efficacy of the Percutaneous Transvenous Mitral Annuloplasty Device (PTOLEMY), http://clinicaltrials.gov/ct2/show/NCT00571610?term=mitral+regurgitation&rank=13, Aug. 25, 2008, 1-4.
ClinicalTrials.gov, Pivotal Study of a Percutaneous Mitral Valve Repair System, http://clinicaltrials.gov/ct2/show/NCT00209274?term=mitral+valve&rank=1, Aug. 25, 2008, 1-4.
ClinicalTrials.gov, RESTOR-MV: Randomized Evaluation of a Surgical Treatment for Off-Pump Repair of the Mitral Valve, http://clinicaltrials.gov/ct2/show/NCT00120276?term=myocor&rank=1, Aug. 25, 2008, 1-5.
ClinicalTrials.gov, Safety and Efficacy of the Percutaneous Transvenous Mitral Annuloplasty Device to Reduce Mitral Regurgitation (PTOLEMY), http://clinicaltrials.gov/ct2/show/NCT00568230?term=mitral+valve&rank=53, Aug. 25, 2008, 1-3.
ClinicalTrials.gov, VIVID-Valvular and Ventricular Improvement Via iCoapsys Delivery—Feasibility Study, http://clinicaltrials.gov/ct2/show/NCT00512005?term=mitral+valve&rank=12, Aug. 25, 2008, 1-4.
Crabtree et al., Recurrent Mitral Regurgitation and Risk Factors for Early and Late Mortality After Mitral Valve Repair for Functional Ischemic Mitral Regurgitation, The Society of Thoracic Surgeons, 2008, 1537-43, 85.
Criber et al., Early Experience With Percutaneous Transcatheter Implantation of Heart Valve Prosthesis for the Treatment of End-Stage Inoperable Patients With Calcific Aortic Stenosis, Journal of the American College of Cardiology, Feb. 18, 2004, 698-703, vol. 43, No. 4.
De Bonis et al., Similar long-term results of mitral valve repair for anterior compared with posterior leaflet prolapse, The Journal of Thoracic and Cardiovascular Surgery, Feb. 2006, 364-370, vol. 131, No. 2.
Deloche et al., Valve repair with Carpentier techniques the second decade, The Journal of Thoracic and Cardiovascular Surgery, Jun. 1990, 990-1002, vol. 99, No. 6.
De Simone et al., A clinical study of annular geometry and dynamics in patients with ischemic mitral regurgitation: new insights into asymmetrical ring annuloplasty, European Journal of Cardio-thoracic Surgery, 2006, 355-361, 29.
Detaint et al., Surgical Correction of Mitral Regurgitation in the Elderly—Outcomes and Recent Improvements, Downloaded from circ.ahajournals.org, Aug. 26, 2008, 265-272.
Dubreuil et al., Percutaneous Mitral Valve Annuloplasty for Ischemic Mitral Regurgitation: First in Man Experience With a Tempory Implant, Catheterization and Cardiovascular Interventions, 2007, 1053-61, 69.
Duffy et al., Feasibility and Short-Term Efficacy of Percutaneous Mitral Annular Reduction for the Therapy of Funcitonal Mitral Regurgitation in Patients With Heart Failure, Catheterization and Cardiovascular Interventions, 2006, 205-210, 68.
Epstein et al., Gross and Microscopic Pathological Changes Associated With Nonthoracotomy Implantable Defibrillator Leads, Downloaded from circ.ahajournals.org, Jul. 23, 2008, 1517-24.

Epstein et al., Embolic Complications Associated With Radiofrequency Catheter Ablation, The American Journal of Cardiology, Mar. 15, 1996, 655-658, vol. 77.

Fagundes et al., Safety of Single Transseptal Puncture for Ablation of Atrial Fibrillation: Retrospective Study from a Large Cohort of Patients, Journal of Cardiovascular Electrophysiology, Dec. 2007, 1277-81, vol. 18, No. 12.

Feldman et al., Patient selection for percutaneous mitral valve repair: insight from early clinical trial applications, Nature Clinical Practice Cardiovascular Medicine, Feb. 2008, 84-90, vol. 5, No. 2.

Feldman et al., Percutaneous Mitral Valve Repair Using the Edge-to-Edge Technique—Six-Month Results of the Everest Phase I Clinical Trial, Journal of the American College of Cardiology, Dec. 6, 2005, 2134-40, vol. 46, No. 11.

Fernandez et al., Early and late-phase events after valve replacement with the St. Jude Medical prosthesis in 1200 patients, The Journal of Thoracic and Cardiovascular Surgery, Feb. 1994, 394-407, vol. 107, No. 2.

Gillinov et al., Durability of Mitral Valve Repair for Degenerative Disease, The Journal of Thoracic and Cardiovascular Surgery, Nov. 1998, 734-743, vol. 116, No. 5.

Grossi et al., Intraoperative Effects of the Coapsys Annuloplasty System in a Randomized Evaluation (RESTOR-MV) of Functional Ischemic Mitral Regurgitation, The Society of Thoracic Surgeons, 2005, 1706-11, 80.

Grossi et al., Late Results of Mitral Valve Reconstruction in the Elderly, The Society of Thoracic Surgeons, 2000, 1224-6, 70.

Grossi et al., Minimally Invasive Mitral Valve Surgery: A 6-Year Experience With 714 Patients, The Society of Thoracic Surgeons, 2002, 660-4, 74.

Hendren et al., Mitral Valve Repair for Ischemic Mitral Insufficiency, The Society of Thoracic Surgeons, 1991, 1246-52, 52.

Heupler et al., Infection Prevention Guidelines for Cardiac Catheterization Laboratories, Catheterization and Cardiovascular Diagnosis, 1992, 260-263, 25.

Hvass et al., Papillary Muscle Sling: A New Functional Approach to Mitral Repair in Patients With Ischemic Left Ventricular Dysfunction and Functional Mitral Regurgitation, The Society of Thoracic Surgeons, 2003, 809-11, 75.

Ibrahim et al., The St. Jude Medical prosthesis—A thirteen-year experience, The Journal of Thoracic and Cardiovascular Surgery, Aug. 1994, 221-230, vol. 108, No. 2.

Iskandar et al., Tricuspid Valve Malfunction and Ventricular Pacemaker Lead: Case Report and Review of the Literature, Echocardiography: A Jrnl of CV Ultrasound & Allied Tech., 2006, 692-697, vol. 23, No. 8.

Kasegawa et al., Mitral Valve Repair for Anterior Leaflet Prolapse With Expanded Polytetrafluoroethylene Sutures, The Society of Thoracic Surgeons, 2006, 1625-31, 81.

Kaye et al., Feasibility and Short-Term Efficacy of Percutaneous Mitral Annular Reduction for the Therapy of Heart Failure-Induced Mitral Regurgitation, Downloaded from circ.ahajournals.org, Aug. 26, 2008, 1795-97.

International Search Report and Written Opinion dated Sep. 22, 2008 issued in PCT Application No. PCT/US08/63560, 11 pages.

International Search Report and Written Opinion dated Sep. 29, 2008 issued in PCT Application No. PCT/US08/63568, 12 pages.

Kerensky, Complications of Cardiac Catheterization and Strategies to Reduce Risks, Diagnostic and Therapeutic Cardiac Catheterization, 1998, Chapter 8, 91-105.

Koertke et al., INR Self-Management Permits Lower Anticoagulation Levels After Mechanical Heart Valve Replacement, downloaded from circ.ahajournals.org, Aug. 26, 2008, II-75-II-78.

Kratz et al., St. Jude Prosthesis for Aortic and Mitral Valve Replacement: A Ten-Year Experience, The Society of Thoracic Surgeons, 1993, 462-8, 56.

Kron et al., Surgical Relocation of the Posterior Papillary Muscle in Chronic Ischemic Mitral Regurgitation, The Society of Thoracic Surgeons, 2002, 600-1, 74.

Kuwahara et al., Mechanism of Recurrent/Persistent Ischemic/Functional Mitral Regurgitation in the Chronic Phase After Surgical Annuloplasty—Importance of Augmented Posterior Leaflet Tethering, Circulation, Jul. 4, 2006, I-529-I-534.

Laskey et al., Multivariable Model for Prediction of Risk of Significant Complication During Diagnostic Cardiac Catheterization, Catheterization and Cardiovascular Diagnosis, 1993, 185-190, 30.

Lee et al., Mitral Valve Reconstruction: Experience Related to Early and Late Mortality and Reoperation, J Heart Valve Dis, Nov. 2005, 715-721, vol. 14, No. 6.

Liddicoat et al., Percutaneous Mitral Valve Repair: A Feasibility Study in an Ovine Model of Acute Ischemic Mitral Regurgitation, Catheterization and Cardiovascular Interventions, 2003, 410-416, 60.

Lim et al., Percutaneous Transthoracic Ventricular Puncture for Diagnostic and Interventional Catheterization, Catheterization and Cardiovascular Interventions, 2008, 915-918, 71.

Lin et al., Severe Symptomatic Tricuspid Valve Regurgitation Due to Permanent Pacemaker or Implantable Cardioverter-Defibrillator Leads, Journal of the American College of Cardiology, May 17, 2005, 1672-5, vol. 45, No. 10.

Lozonschi et al., Transapical Mitral Valved Stent Implantation, The Society of Thoracic Surgeons, 2008, 745-8, 86.

Mack, Percutaneous Therapies for Mitral Regurgitation: Where Do We Stand and Where Are We Going? Do Current Devices Really Represent a Step Forward Compared to Surgery?, 2007 Heart Valve Summit, Jun. 7, 2007, 59 pages.

Maleki et al., Intracardiac Ultrasound Detection of Thrombus on Transseptal Sheath: Incidence, Treatment, and Prevention, Journal of Cardiovascular Electrophysiology, Jun. 2005, 561-565, vol. 16, No. 6.

Maniu et al., Acute and Chronic Reduction of Functional Mitral Regurgitation in Experimental Heart Failure by Percutaneous Mitral Annuloplasty, Journal of the American College of Cardiology, Oct. 19, 2004, 1652-61, vol. 44, No. 8.

McGee et al., Recurrent mitral regurgitation after annuloplasty for functional ischemic mitral regurgitation, Surgery for Acquired Cardiovascular Disease, The Journal of Thoracic and Cardiovascular Surgery, Dec. 2004, 916-924.e4, vol. 128, No. 6.

Mehra et al., Surgery for Severe Mitral Regurgitation and Left Ventricular Failure: What Do We Really Know?, Journal of Cardiac Failure, Mar. 2008, 145-150. vol. 14, No. 2.

Menicanti et al., Functional Ischemic Mitral Regurgitation in Anterior Ventricular Remodeling: Results of Surgical Ventricular Restoration with and Without Mitral Repair, Heart Failure Reviews, 2004, 317-327, 9.

Messas et al., Efficacy of Chordal Cutting to Relieve Chronic Persistent Ischemic Mitral Regurgitation, Circulation, Sep. 9, 2003, II-111-II-115.

Meurin et al., Thromboembolic events early after mitral valve repair: Incidence and predictive factors, International Journal of Cardiology, 2008, 45-52, 126.

Mirable et al., What are the characteristics of patients with severe, symptomatic, mitral regurgitation who are denied surgery?, The European Society of Cardiology, 2007, 1358-65, 28.

Mitchell et al., Complications, Cardiac catheterization and coronary intervention, Chapter 9, 2008, 238-270.

Mishra et al., Coapsys Mitral Annuloplasty for Chronic Functional Ischemic Mitral Regurgitation: 1-Year Results, The Society of Thoracic Surgeons, 2006, 42-46, 81.

Morgan et al., Left Heart Catheterization by Direct Ventricular Puncture: Withstanding the Test of Time, Catheterization and Cardiovascular Diagnosis, 1989, 87-90, 16.

Murday et al., A Prospective Controlled Trial of St. Jude Versus Starr Edwards Aortic and Mitral Valve Prostheses, The Society of Thoracic Surgeons, 2003, 66-74, 76.

Nifong et al., Robotic mitral valve surgery: A United States multicenter trial, The Journal of Thoracic and Cardiovascular Surgery, Jun. 2005, 1395-1404, vol. 129, No. 6.

Noto et al., Cardiac Catheterization 1990: A Report of the Registry of the Society for Cardiac Angiography and Interventions (SCA&I), Catheterization and Cardiovascular Diagnosis, 1991, 75-83, 24.

Ohlow et al., Incidence and outcome of femoral vascular complications among 18,165 patients undergoing cardiac catheterisation, International Journal of Cardiology, 2008, 1-6.

Piazza et al., Transcatheter Mitral Valve Repair for Functional Mitral Regurgitation: Coronary Sinus Approach, Journal of Interventional Cardiology, 2007, 495-508, vol. 20, No. 6.
Pedersen et al., iCoapsys Mitral Valve Repair System: Percutaneous Implantation in an Animal Model, Catheterization and Cardiovascular Interventions, 2008, 125-131, 72.
Prifti et al., Ischemic Mitral Valve Regurgitation Grade II-III: Correction in Patients with Impaired Left Ventricular Function undergoing Simultaneous Coronary Revascularization, J Heart Valve Dis, Nov. 2001, 754-762, vol. 10, No. 6.
Richardson et al., Is a port-access mitral valve repair superior to the sternotomy approach in accelerating postoperative recovery?, Interactive CardioVascular and Thoracic Surgery, Downloaded from icvts.ctsnetjournals.org, Aug. 26, 2008, 670-683, 7.
Ruiz, New Percutaneous Approaches for Mitral Regurgitation, Lenox Hill Heart and Vascular Institute of New York, May 13-16, 2008, 26 pages.
Rumel et al., Section on Cardiovascular Diseases—The Correction of Mitral Insufficiency With a Trans-Valvular Polyvinyl Formalinized Plastic (Ivalon) Sponge Prosthesis, American College of Chest Physicians, Apr. 1958, Downloaded from chestjournal.org, Jul. 23, 2008, 401-413.
Seeburger et al., Minimal invasive mitral valve repair for mitral regurgitation: results of 1339 consecutive patients, European Journal of Cardio-thoracic Surgery, 2008, 1-6.
Southard et al., Current Catheter-Based Treatments of Functional Mitral Regurgitation, Cardiac Interventions Today, Jun. 2007, 41-44.
Svensson et al., United States Feasibility Study of Transcatheter Insertion of a Stented Aortic Valve by the Left Ventricular Apex, The Society of Thoracic Surgeons, 2008, 46-55, 86.
Toledano et al., Mitral regurgitation: Determinants for referral for cardiac surgery by Canadian cardiologists, Can J. Cardiol, Mar. 1, 2007, 209-214, vol. 23, No. 3.
Tops et al., Percutaneous Valve Procedures: An Update, Curr Probl Cardiol, Aug. 2008, 417-426.
Walther et al., Transapical minimally invasive aortic valve implantation; the initial 50 patients, European Journal of Cardio-thoracic Surgery, 2008, 983-988, 33.
Webb et al., Percutaneous Mitral Annuloplasty With the Monarc System: Preliminary Results From the Evolution Trial, TCT-103, The American Journal of Cardiology, Oct. 22-27, 2006, 49M.
Webb et al., Percutaneous Transvenous Mitral Annuloplasty—Initial Human Experience with Device Implantation in the Coronary Sinus, downloaded from circ.ahajournals.org, Aug. 26, 2008, 851-855.
Webster et al., Impact of transvenous ventricular pacing leads on tricuspid regurgitation in pediatric and congenital heart disease patients, J Interv Card Electrophysiol, 2008, 65-68, 21.
Ye et al., Six-month outcome of transapical transcatheter aortic valve implantation in the initial seven patients, European Journal of Cardio-thoracic Surgery, 2007, 16-21, 31.
Yoshida, et al., Assessment of Left-to-Right Atrial Shunting After Percutaneous Mitral Valvuloplasty by Transesophageal Color Doppler Flow-Mapping, Circulation, Dec. 1989, 1521-1526, vol. 80, No. 6.
Zhou et al., Thromboembolic Complications of Cardiac Radiofrequency Catheter Ablation: A Review of the Reported Incidence, Pathogenesis and Current Research Directions, Journal of Cardiovascular Electrophysiology, Apr. 1999, 611-620, vol. 10, No. 4.
U.S. Office Action dated Jul. 8, 2009 issued in U.S. Appl. No. 11/258,828, 7 pages.
International Search Report and Written Opinion dated Aug. 11, 2009 issued in PCT Application No. PCT/US2009/046995, 11 pages.
U.S. Office Action dated Sep. 29, 2009 issued in U.S. Appl. No. 12/209,686, 9 pages.
European Search Report dated Jul. 12, 1984 cited in EP0125393.
"French catheter scale chart" http://en.wikipedia.org/wiki/French_catheter_scale_chart, Dec. 20, 2006, 1 page.
"General Physical Properties of PVA Sponge (values are not guaranteed)", Ceiba Technologies, http://www.ceibatech.com/PVASpongeDate.htm, Dec. 20, 2006 3 pages.
"PVA Datasheet", www.sponge-pva.com/data.htm, Dec. 20, 2006, 2 pages.
"PVA Sponge W (wet) & D (dry)", Ceiba Technologies, http://www.ceibatech.com/PVASpongeW&D.htm, Dec. 20, 2007 5 pages.
SPI-Chem™ Vinylec® (Formvar®) Resins, http://www.2spi.com/catalog/submat/formvar-resins.shtml, Dec. 20, 2006, 5 pages.
"Vinylec® Resins", http://www.2spi.com/catalog/submat/vinylec-physical.html, Dec. 20, 2006, 1 page.
U.S. Office Action dated Dec. 15, 2009 issued in U.S. Appl. No. 11/258,828, 12 pages.
U.S. Office Action dated Jan. 8, 2010 issued in U.S. Appl. No. 11/748,147, 63 pages.
U.S. Office Action dated Jan. 14, 2010 issued in U.S. Appl. No. 11/940,674, 59 pages.
U.S. Office Action dated Jan. 25, 2010 issued in U.S. Appl. No. 11/748,121, 9 pages.
U.S. Office Action dated Jun. 2, 2010 issued in U.S. Appl. No. 12/209,686, 15 pages.
U.S. Office Action dated Jun. 28, 2010 issued in U.S. Appl. No. 11/258,828, 14 pages.
Notice of Allowance dated Jul. 1, 2010 issued in U.S. Appl. No. 11/940,674, 6 pages.
U.S. Office Action dated Jul. 20, 2010 issued in U.S. Appl. No. 11/748,147, 15 pages.
Ryhänen et al., In vivo biocompatibility evaluation of nickel-titanium shape memory metal alloy: Muscle and perineural tissue responses and encapsule membrane thickness, Muscle and Perineural Tissue Response to Nitinol, Jan. 19, 1998, pp. 481-488.
International Search Report and Written Opinion dated Jul. 6, 2010 issued in PCT Patent Application No. PCT/US2010/032764, 9 pages.
Extended European Search Report dated Dec. 1, 2010 issued in European Patent Application No. 08755426.7, 6 pages.
Extended European Search Report dated Dec. 14, 2010 issued in European Patent Application No. 06816336.9, 7 pages.
U.S. Office Action dated Mar. 21, 2011 issued in U.S. Appl. No. 11/258,828, 22 pages.
U.S. Office Action dated Mar. 29, 2011 issued in U.S. Appl. No. 11/748,121, 14 pages.
U.S. Office Action dated Apr. 4, 2011 issued in U.S. Appl. No. 11/940,724, 65 pages.
European Examination Report dated Aug. 4, 2011 issued in European Patent No. 06 816 336.9, 3 pages.
U.S. Office Action dated Aug. 29, 2011 issued in U.S. Appl. No. 11/940,694, 11 pages.
European Examination Report dated Aug. 11, 2011 issued in European Patent No. 08 755 418.4, 3 pages.
U.S. Office Action dated Sep. 19, 2012, issued in U.S. Appl. No. 12/510,929, 10 pages.
U.S. Office Action dated Oct. 9, 2012, issued in U.S. Appl. No. 12/872,228, 7 pages.
U.S. Notice of Allowance dated Nov. 21, 2012, issued in U.S. Appl. No. 11/748,121, 8 pages.
Notice of Allowance dated Oct. 31, 2011 issued in U.S. Appl. No. 11/258,828, 10 pages.
Preliminary Report on Patentability dated Nov. 1, 2011 issued in PCT Patent Application No. PCT/US2010/032764, 4 pages.
U.S. Office Action dated Nov. 3, 2011 issued in U.S. Appl. No. 12/872,228, 8 pages.
Notice of Allowance dated Dec. 14, 2011 issued in U.S. Appl. No. 12/431,399, 12 pages.
U.S. Office Action dated Dec. 21, 2011, issued in U.S. Appl. No. 11/748,121, 9 pages.
U.S. Office Action dated Jan. 18, 2012 issued in U.S. Appl. No. 11/940,724, 10 pages.
Extended European search report dated Nov. 30, 2010 issued in European Patent Application No. 08850467.5, 6 pages.
Extended European search report dated Nov. 30, 2010 issued in European Patent Application No. 08755418.4, 7 pages.
Extended European search report dated Nov. 30, 2010 issued in European Patent Application No. 08849442.2, 6 pages.
U.S. Office Action dated Jun. 20, 2012 issued in U.S. Appl. No. 11/940,694, 9 pages.
U.S. Office Action dated Jun. 21, 2012 issued in U.S. Appl. No. 11/748,147, 29 pages.

Notice of Allowance dated Jul. 20, 2012 issued in U.S. Appl. No. 11/748,121, 10 pages.
International Preliminary Report on Patentability dated Jan. 31, 2012 issued in PCT Patent Application No. PCT/US2010/043360, 7 pages.
U.S. Office Action dated Feb. 15, 2012 issued in U.S. Appl. No. 11/940,694, 9 pages.
U.S. Notice of Allowance dated Mar. 8, 2012 issued in U.S. Appl. No. 12/872,228, 7 pages.
Canadian Office Action dated Sep. 18, 2012 issued in Canadian Patent Application No. 2,627,517, 2 pages.
Intent to Grant dated Jan. 2, 2013 issued in European Patent Application No. 06816336.9, 7 pages.
Notice of Allowance dated Jan. 9, 2013 issued in U.S. Appl. No. 11/748,121, 7 pages.
U.S. Office Action dated Aug. 31, 2010 issued in U.S. Appl. No. 11/748,121, 11 pages.
International Search Report and Written Opinion dated Sep. 21, 2010 issued in PCT Patent Application No. PCT/US2010/043360, 9 pages.
Final Office Action dated Mar. 13, 2013 issued in U.S. Appl. No. 11/748,147, 10 pages.
Final Office Action dated Mar. 22, 2013 issued in U.S. Appl. No. 12/510,929, 13 pages.
Notice of Allowance dated Apr. 11, 2013 issued in U.S. Appl. No. 13/545,927, 12 pages.
Supplemental Notice of Allowability dated May 2, 2013 issued in U.S. Appl. No. 13/545,927, 5 pages.
European Intent to Grant dated Feb. 22, 2013 issued in European Patent Application No. 08 755 418.4, 7 pages.
European Search Report dated Mar. 6, 2013 issued in European Patent Application No. 10804952.9, 8 pages.

* cited by examiner

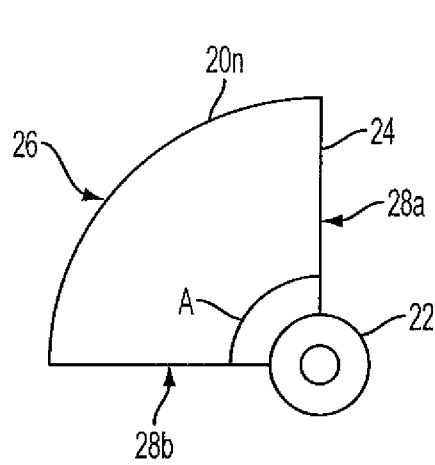
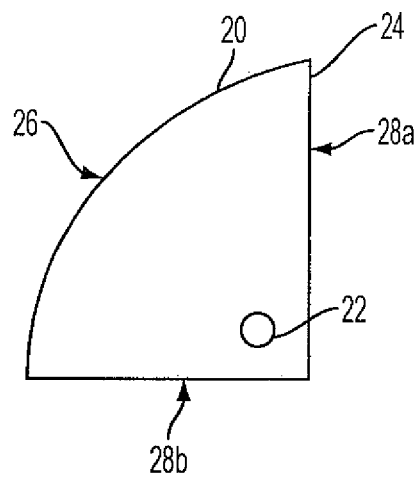
FIG. 5    FIG. 6
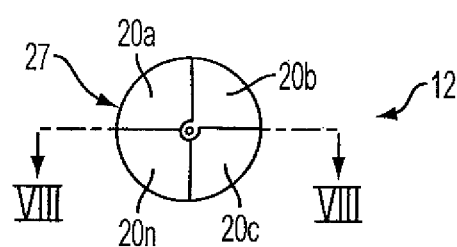
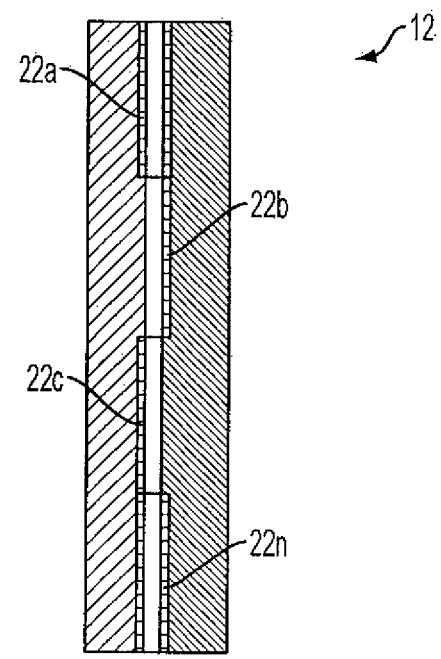
FIG. 7    FIG. 8

SOLID CONSTRUCT MITRAL SPACER

FIELD

The present disclosure relates to the repair and/or correction of dysfunctional heart valves, and more particularly pertains to heart valve implants and systems and methods for delivery and implementation of the same.

BACKGROUND

A human heart has four chambers, the left and right atrium and the left and right ventricles. The chambers of the heart alternately expand and contract to pump blood through the vessels of the body. The cycle of the heart includes the simultaneous contraction of the left and right atria, passing blood from the atria to the left and right ventricles. The left and right ventricles then simultaneously contract forcing blood from the heart and through the vessels of the body. In addition to the four chambers, the heart also includes a check valve at the upstream end of each chamber to ensure that blood flows in the correct direction through the body as the heart chambers expand and contract. These valves may become damaged, or otherwise fail to function properly, resulting in their inability to properly close when the downstream chamber contracts. Failure of the valves to properly close may allow blood to flow backward through the valve resulting in decreased blood flow and lower blood pressure.

Mitral regurgitation is a common variety of heart valve dysfunction or insufficiency. Mitral regurgitation occurs when the mitral valve separating the left coronary atrium and the left ventricle fails to properly close. As a result, upon contraction of the left ventricle blood may leak or flow from the left ventricle back into the left atrium, rather than being forced through the aorta. Any disorder that weakens or damages the mitral valve can prevent it from closing properly, thereby causing leakage or regurgitation. Mitral regurgitation is considered to be chronic when the condition persists rather than occurring for only a short period of time.

Regardless of the cause, mitral regurgitation may result in a decrease in blood flow through the body (cardiac output). Correction of mitral regurgitation typically requires surgical intervention. Surgical valve repair or replacement is carried out as an open heart procedure. The repair or replacement surgery may last in the range of about three to five hours, and is carried out with the patient under general anesthesia. The nature of the surgical procedure requires the patient to be placed on a heart-lung machine. Because of the severity/complexity/danger associated with open heart surgical procedures, corrective surgery for mitral regurgitation is typically not recommended until the patient's ejection fraction drops below 60% and/or the left ventricle is larger than 45 mm at rest.

BRIEF DESCRIPTION OF THE DRAWINGS

Features and advantage of the claimed subject matter will be apparent from the following description of embodiments consistent therewith, which description should be considered in conjunction with the accompanying drawings, wherein:

FIG. 5 is an end view of one embodiment of the spacer segment consistent with the mitral valve implant according to the present disclosure;

FIG. 6 is an end view of another embodiment of the spacer segment consistent with the mitral valve implant according to the present disclosure;

FIG. 7 is an end view of one embodiment of the spacer consistent with the mitral valve implant according to the present disclosure;

FIG. 8 is a cross-sectional view of the spacer shown in FIG. 7 taken along lines VIII-VIII;

DESCRIPTION

Figure 1:
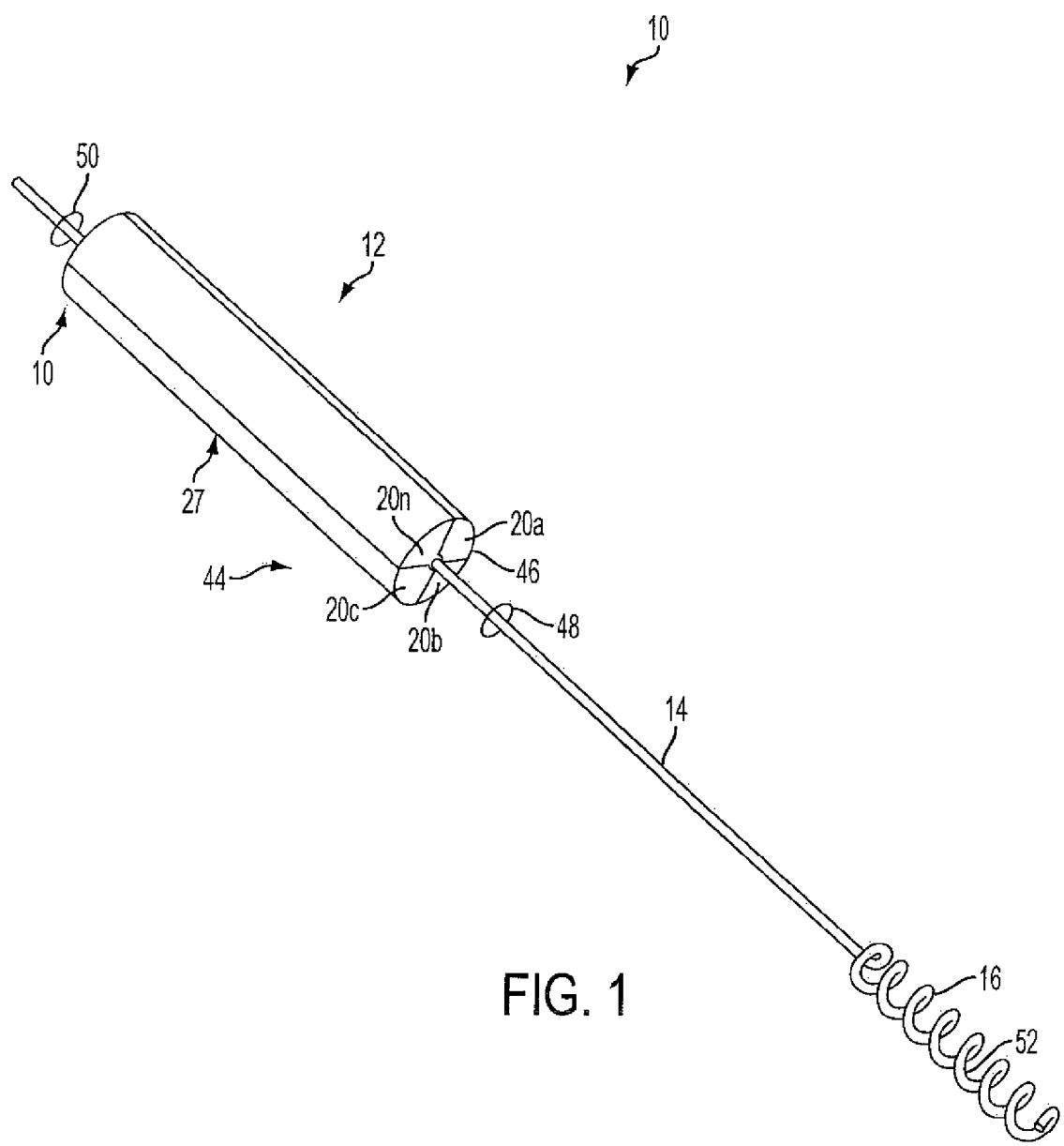
FIG. 1 is a perspective view of an embodiment of a mitral valve implant consistent with the present disclosure.
Figure 2:
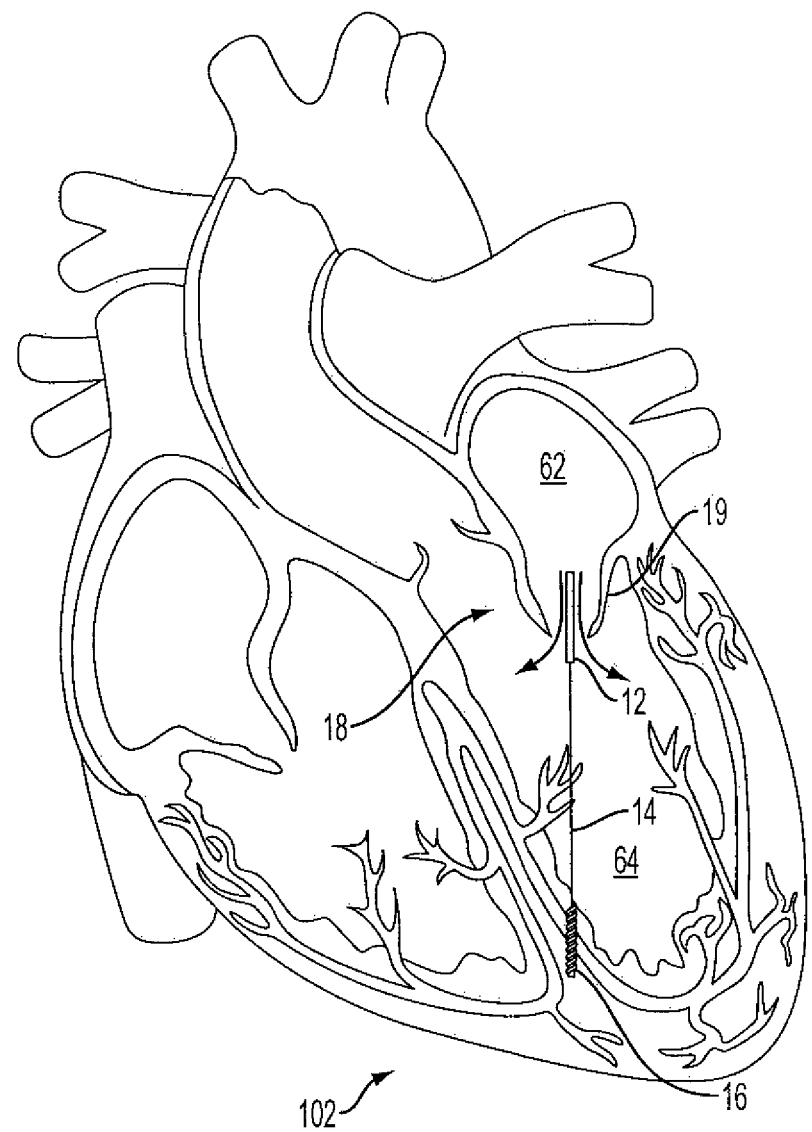
FIG. 2 depicts an embodiment mitral valve implant consistent with the present disclosure implanted within a heart in an open position.
Figure 3:
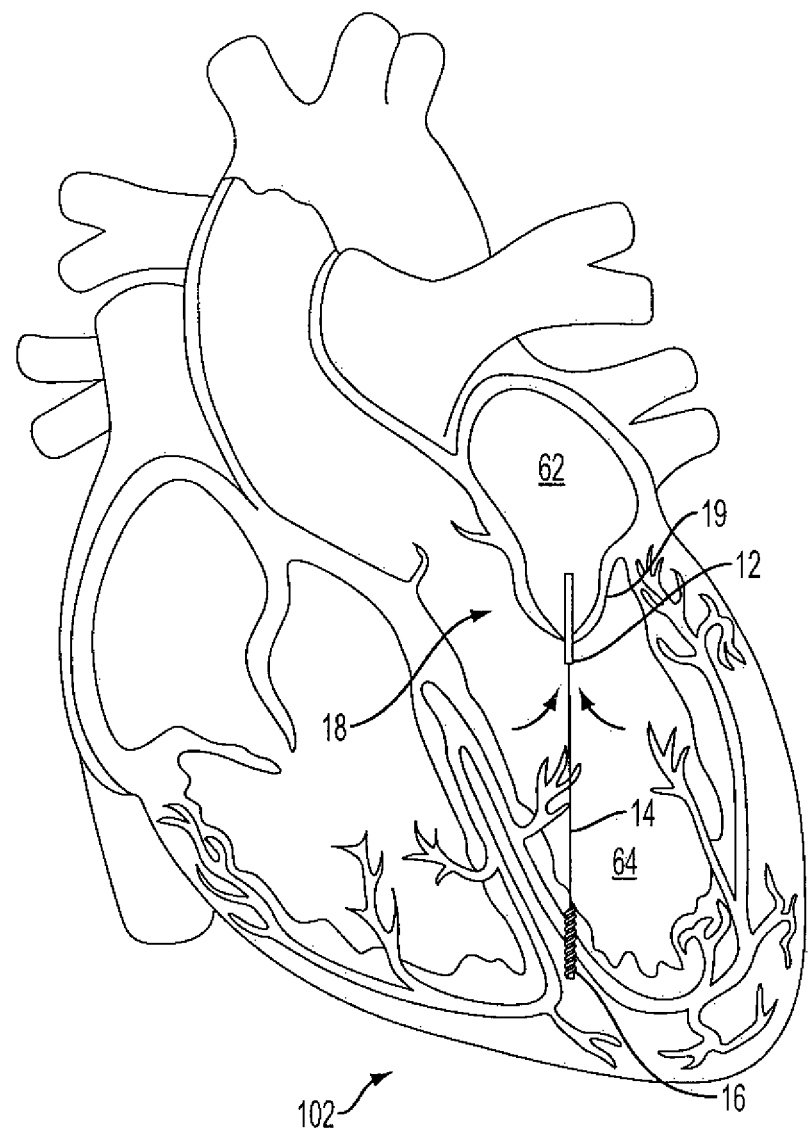
FIG. 3 depicts an embodiment mitral valve implant consistent with the present disclosure implanted within a heart in a closed position.

Referring to FIG. 1, a perspective view of one embodiment of a mitral valve implant 10 is depicted. As shown, mitral valve implant 10 may generally include a spacer or valve body portion 12 which may be coupled to a shaft 14. The shaft 14 may be coupled to at least one anchor portion 16 configured to couple, attach, and/or otherwise secure the mitral valve implant 10 to native coronary tissue. In general, at least a portion of the spacer 12 may be configured to be disposed proximate a mitral valve such that the mitral valve implant 10 may interact and/or cooperate with at least a portion of the native mitral valve to reduce and/or eliminate excessive regurgitation as illustrated in FIGS. 2 and 3.

The spacer 12 of the mitral valve implant 10 shown in FIG. 1 may include a plurality of individual segment 20a-20n. As will be explained in greater detail hereinbelow, the plurality of segments 20a-20n may be configured to be delivered and assembled proximate an implant site of the mitral valve implant 10 to form a spacer 12 having an overall size and shape configured to accommodate, at least in part, a patient's anatomy, etiology of valve regurgitation, and/or the limitations of the implant delivery system. Each of the plurality of segments 20a-20n may be configured to have a size and shape such that at least one dimension of the segment 20a-20n is no larger than at least one internal dimension of the implant delivery system used to deliver the mitral valve implant 10 to the implant site. As such, a mitral valve implant 10 may be constructed having a spacer 12 with at least one cross-sectional dimension that is larger than the internal cross-sectional dimensions of the implant delivery system used to deliver the mitral valve implant 10.

Figure 4:
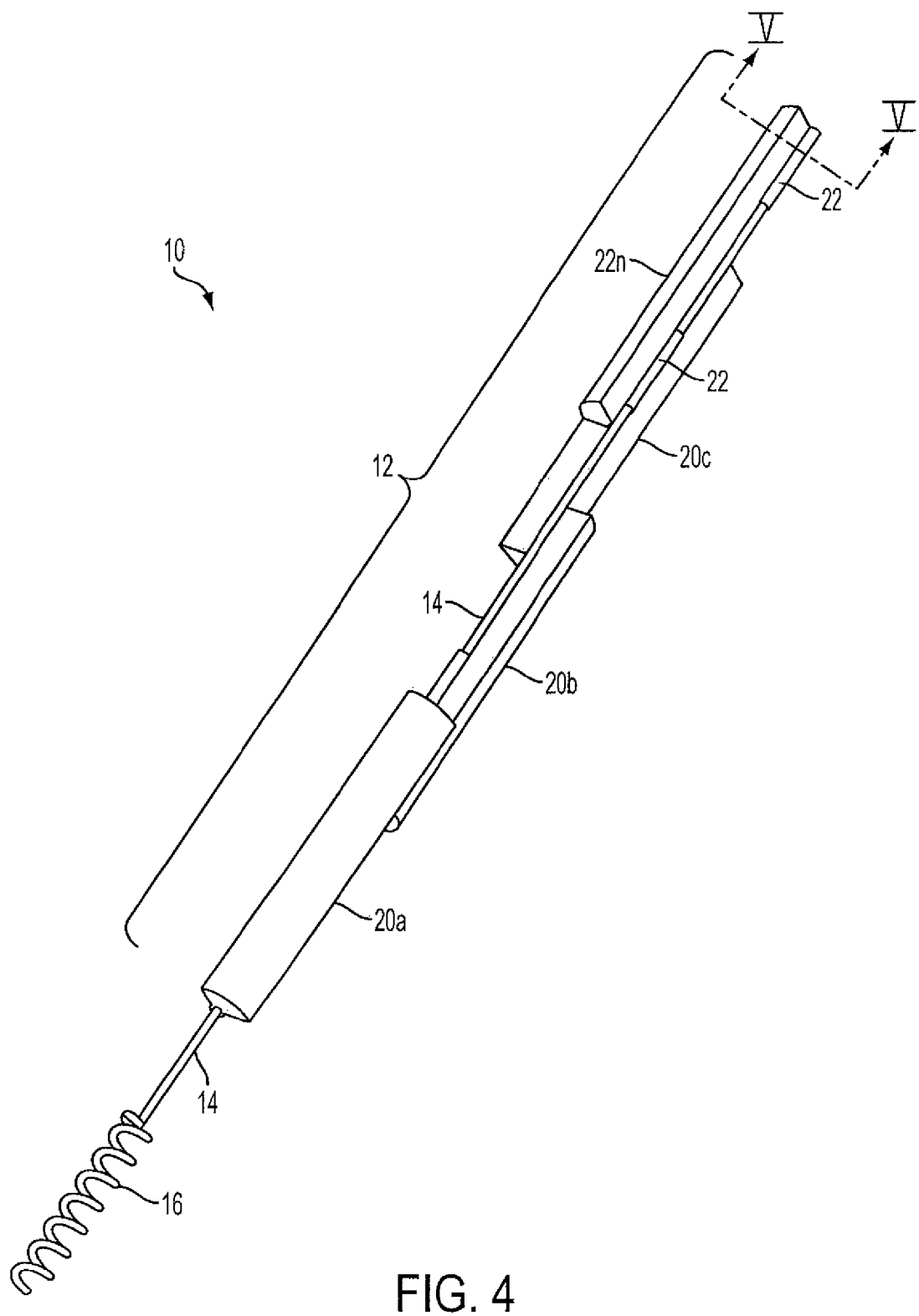
FIG. 4 is a perspective view of the mitral valve implant shown in FIG. 1 in an unassembled state consistent with the present disclosure.
Figure 9A:
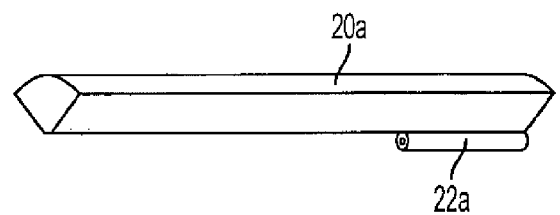
FIG. 9 depict various arrangements of the spacer segments of a mitral valve implant consistent with the present disclosure.
Figure 9B:
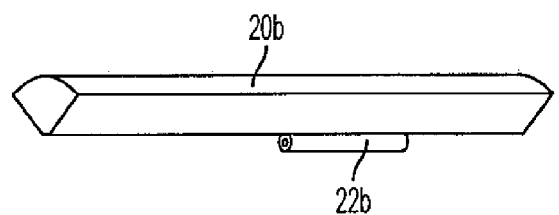
Figure 9C:
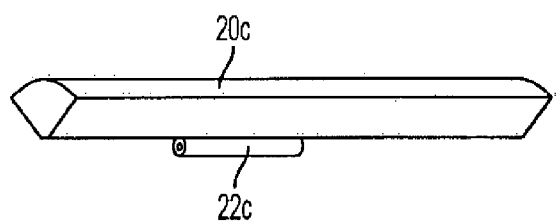
Figure 9D:
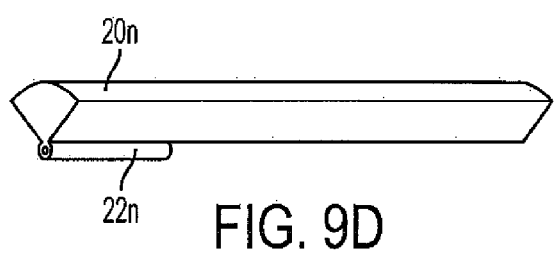
Figure 9E:
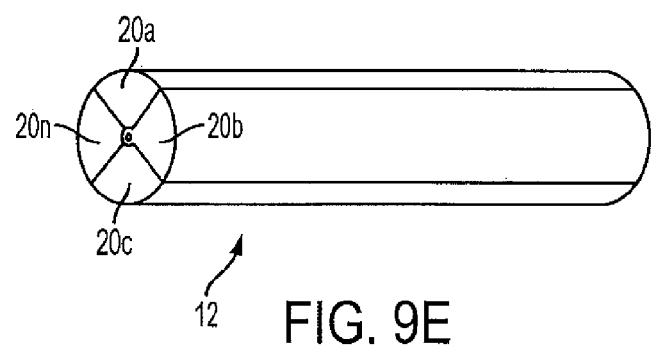

According to one aspect, the mitral valve implant 10 and the spacer 12 is shown in an unassembled/partially assembled state in FIG. 4. The plurality of segments 20a-20n may be slidably coupled over at least a portion of the shaft 14. For example, the plurality of segments 20a-20n may each include at least one passageway 22 configured to accept at least a portion of the shaft 14. As illustrated, one or more of the passageways 22 may define a generally cylindrical opening or passageway having an internal dimension (e.g., an internal radius) substantially corresponding to the outer radius of a generally cylindrical shaft 14. The internal dimension of the passageway 22 may sufficiently greater than the outer radius of the shaft 14 such that the plurality of segments 20a-20n may move along a non-linear shaft 14. In other words, the internal radius of the passageway 22 may be large enough such that the plurality of segments 20a-20n may move along the longitudinal length of a non-linear or curved shaft 14. The passageways 22 may be configured to generally extend completely around the circumference of the shaft 14 and/or may be configured to generally extend only around a portion of the circumference of the shaft 14.

Those skilled in the art will recognize that the passageways 22 and/or the shaft 14 may have a shape other than a cylinder. For example, the passageways 22 and/or the shaft 14 may have a non-circular cross-section such as, but not limited to, an oval or elliptical cross-section or the like. For example, the passageways 22 and/or the shaft 14 may form a lock-and-key type arrangement configured to prevent the segments 20a-20n from rotating about radial direction of the shaft 14.

Referring to FIG. 5, a cross-section of segment 22n of FIG. 4 is shown. The body 24 of segment 22n may include an outer surface 26 which may define at least a portion of the outer surface 27 (FIG. 1) of the spacer 12 when assembled and at least one cross-sectional surface 28. According to one aspect, the body 24 may have a generally circular sector or pie-piece cross-section. The passageway 22 may be formed as a separate component from the body 24 and may be coupled, attached, molded, bonded or otherwise secured to the body 24 of the segment 22n. The passageway 22 may also be formed as an integral, unitary, and/or single component with the body 24. According to one aspect, the passageway 22 may be disposed proximate a centerline of the spacer 12. For example, the passageway 22 may be disposed proximate an intersection between the first and the second cross-sectional surfaces 28a, 28b. The passageway 22 may also be disposed within an internal region of the body 24 as shown in FIG. 6.

As mentioned above, the plurality of segments 20a-20n may be constructed to form a spacer 12, FIG. 7, having an outer surface configured to, at least in part, accommodate a patient's anatomy, etiology of valve regurgitation, and the limitations of the implant delivery system. A cross-sectional view of the assembled spacer 12 in FIG. 7 is illustrated in FIG. 8. According to one aspect, the passageways 22a-22n of each of the plurality of segments 20a-2n may be aligned serially along the longitudinal axis of the spacer 12. For example, each of the passageways 22a-22n, FIGS. 9a-9d, may be spaced along the longitudinal axis of each of the plurality of segments 20a-20n. According to this aspect, the passageways 22a-22n do not overlap each other when the plurality of segments 20a-20n are assembled as shown in FIG. 8. The passageways 22a-22n may be evenly spaced along the longitudinal axis of the plurality of segments 20a-20n such that each passageway 22a-22n substantially abuts against at least one adjacent passageway 22a-22n. Such an arrangement aids in the construction of the spacer 12 since the plurality of segments 20a-20n may only fit together in a single configuration. The passageways 22a-22n may also be unevenly spaced along the plurality of segments 20a-20n and/or may at least partially overlap each other. Those skilled in the art will recognize that a variety of geometries and configurations exist depending on the desired overall size and shape of the spacer 12 as well as the dimensional limitations of the implant delivery system.

According to one aspect, at least a portion of the body 24 of one or more of the plurality of segments 20a-20n may be expandable, retractable, collapsible and/or reducible in volume to facilitate percutaneous and/or transluminal delivery of the mitral valve implant 10. In such a manner, one or more of the segments 20a-20n of the mitral valve implant 10 may include a collapsible member, which may be reduced in volume and/or reduced in maximum cross-section during delivery to the heart and/or during placement and/or attachment of the anchor 16 to native coronary tissue. After delivery to the heart, the segments 20a-20n may be expanded, inflated, and/or otherwise increased in volume or size. Accordingly, the mitral valve implant 10 may be delivered to an implantation site via a smaller diameter catheter, and/or via smaller vessels, than would otherwise be required.

The deformable segments 20a-20n may be collapsed to a reduced size, which may, for example, facilitate loading the mitral valve implant 10 into a catheter delivery system. Such a catheter delivery system may be suitable for transluminal delivery of a mitral valve implant 10, including the segments 20a-20n, to the heart as will be explained further below. In addition to being collapsed, the segments 20a-20n may be deformed to facilitate loading into a catheter delivery system. For example, the segments 20a-20n may be collapsed and may be rolled and/or folded to a generally cylindrical shape, allowing the segments 20a-20n to be loaded in a catheter having a circular lumen.

A collapsed and/or rolled or folded segments 20a-20n may be inflated, restoring the segments 20a-20n to expanded configuration. For example, a collapsed and/or rolled or folded segments 20a-20n may be inflated and restored to an expanded configuration once the mitral valve implant 10 has been delivered to the heart and deployed from a catheter delivery system. Inflating the segments 20a-20n may be carried out by introducing a fluid, such as saline, into the at least one cavity of the segments 20a-20n. In addition to a liquid, such as saline, the segments 20a-20n may be inflated with a setting or curable fluid. The setting or curable fluid may set and/or be cured to a solid and/or semi-solid state within the cavity of the segments 20a-20n. An example of such a material may be a thermoset polymer resin, a gel material, such as silicone gel, etc.

At least a portion of the segments 20a-20n may also be constructed from a shape-memory material. For example, at least a portion of the segments 20a-20n may include a shape-memory alloy such as, but not limited to, copper-zinc-aluminum, copper-aluminum-nickel, and nickel-titanium (NiTi) alloys. The shape-memory alloy may include either one-way or two-way shape memory and may be introduced in to the delivery catheter lumen having a shape which does not exceed the interior dimensions of the delivery catheter lumen. For example, the segments 20a-20n may have a generally elongated or generally helical shape. Upon delivery to proximate the mitral valve, the shape-memory segments 20a-20n may be heated to cause the segments 20a-20n to deform into the desired shape for installation.

Alternatively (or in addition), one or more of the plurality of segments 20a-20n may have generally solid geometry. As used herein, the phrases "generally solid geometry," "substantially solid geometry," or the like are intended to mean a geometry having an outer surface that defines a substantially fixed or constant volume. That is, a volume of the segments 20a-20n does not substantially change before and after implantation of the mitral valve implant 10. A "generally solid geometry" may include, without limitation, a solid, semi-solid, or porous (e.g., micro- or nano-scale pores) material. The use a plurality of segments 20a-20n having a generally solid geometry may reduce the complexity and/or cost associated with the fabrication and/or implantation of the mitral valve implant 10 while still allowing a mitral valve implant 10 with a spacer 12 that is at least as large as, or optionally larger than, the implant delivery system used to deliver the mitral valve implant 10.

At least a portion of the plurality of segments 20a-20n may be constructed from a synthetic and/or biological material depending on the application and the patient condition. The segments 20a-20n may include a plurality of layers. For example, the segments 20a-20n may include an open or closed cell foam substrate (for example, but not limited to, Invalon polyvinyl) and an outer layer of a material that is biologically acceptable. The outer layer may also include a material that is soft and/or deformable (either permanently or resiliently deformable) that may reduce and/or eliminate further scarring and/or damage to the leaflets 19 of the mitral valve 18. According to one aspect, the substrate of the segments 20a-20n may be coated with a silicone urethane composite such as, but not limited to, Elasteon or the like.

The plurality of segments 20a-20n, when assembled, may form a spacer 12 having an outer surface 27 that may be configured to interact and/or cooperate with at least a portion of the native mitral valve 18 (e.g., the leaflets 19) to reduce and/or eliminate excessive regurgitation as illustrated in FIGS. 2 and 3. According to one aspect, the mitral valve implant 10 (and in particular, the spacer 12) may be selected from a range or set of sizes and shapes. For example, a "standard set" may be utilized where a set of "consensus" sizes and shapes mitral valve implants 10 are pre-manufactured and provided to health care providers as a kit. This particular aspect has the advantage of being the most uniform and therefore the least expensive for the patient. Alternatively, a "custom design" may be fabricated where the exact size and shape is determined only after precise and/or detailed measurements of the dimensions of a patient's mitral valve 18 are obtained. As a result, the overall size and/or shape of the mitral valve implant 10 may be tapered or shaped if necessary.

Figure 10:
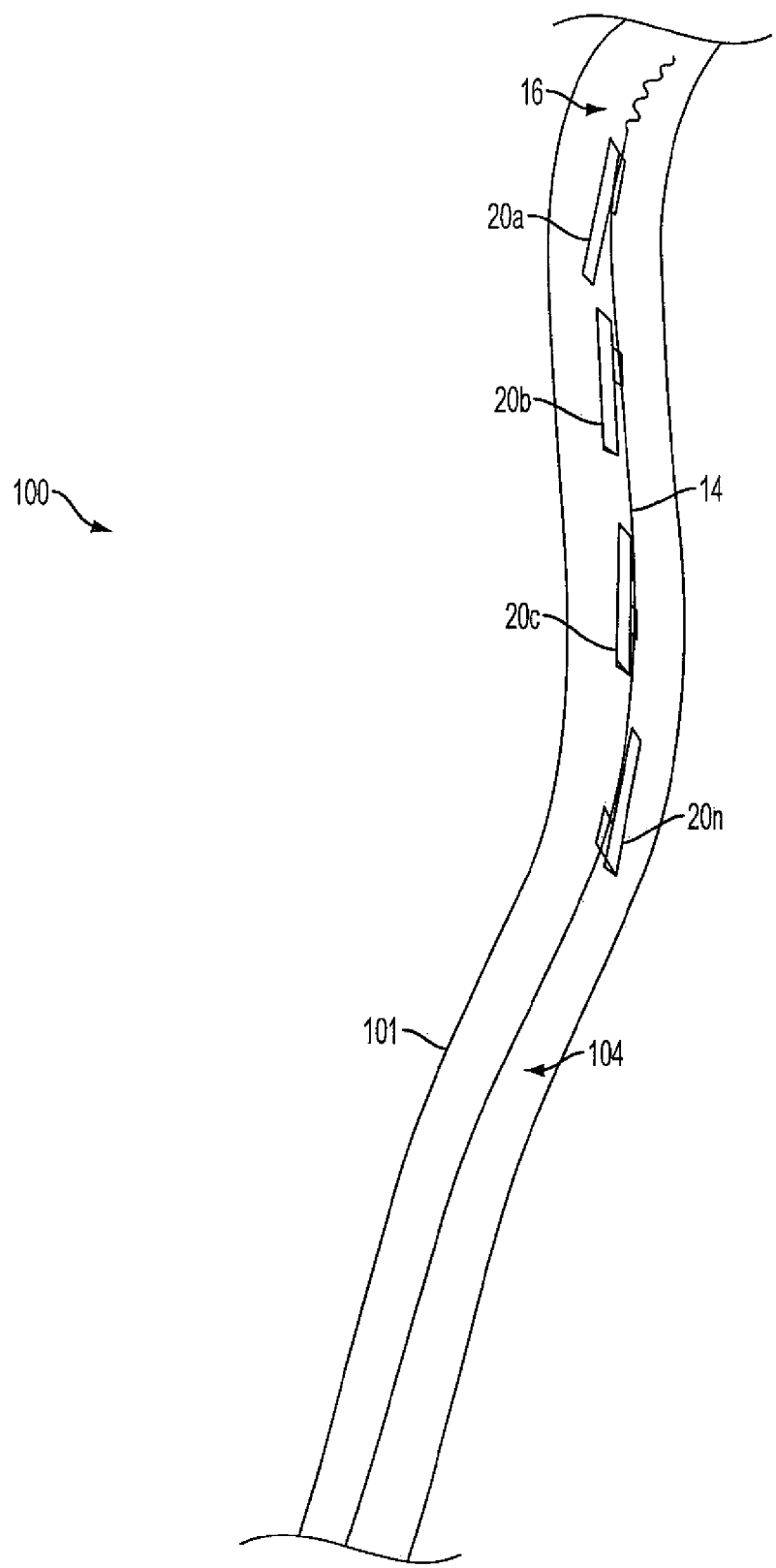
FIG. 10 depicts one embodiment of an implant delivery system consistent with the present disclosure.

In practice, the plurality of segments 20a-20n may be aligned serially along at least a portion of the shaft 14 (i.e., one segment 20a after another segment 20b) and inserted into the implant delivery system 100, a portion of which is generally depicted in FIG. 10. The implant delivery system 100 may include a catheter 101 having a generally circular inner passageway 104. Those skilled in the art will recognize that the catheter 101 may include any catheter known to those skilled in art. While only a single passageway 104 is shown for clarity, the catheter 101 may include a plurality of passageways 104. According to one aspect, the plurality of segments 20a-20n may be rotated about the shaft 14 such that each of the plurality of segments 20a-20n is aligned in a substantially similar or substantially the same orientation with respect to each other. As such, overall cross-sectional dimensions of the mitral valve implant 10 may be minimized. Additionally, the mitral valve implant 10 may be inserted into a catheter 101 having a reduced diameter.

Once loaded into the delivery catheter system 100, the mitral valve implant 10 may be moved or delivered proximate the implant site using any device know to those skilled in the art. While moving the mitral valve implant 10 through the delivery catheter system 100, the plurality of segments 20a-20n may be individually rotated about the shaft 14 to facilitate movement of the plurality of segments 20a-20n. This may be particularly useful to facilitate navigating the plurality of segments 20a-20n about curves, bends or the like 106. The shaft 14 may include a generally rigid shaft and/or a generally flexible shaft.

According to another aspect, shaft 14 and the plurality of segments 20a-20n may be separately loaded into the catheter delivery system 100 and delivered to the implant site. According to this aspect, the shaft 14 (which may optionally include the anchor portion 16) may be first loaded into the catheter delivery system and the plurality of segments 20a-20n may be subsequently serially loaded into the catheter delivery system 100. Of course, the order of loading and/or delivering the shaft 14 and/or plurality of segments 20a-20 to the implant site may be changed.

Once the shaft 14 and the plurality of segments 20a-20n are proximate the implant site, the plurality of segments 20a-20n may be disposed or arranged about the shaft 14 to construct a spacer 12 having a desired size and shape. While the spacer 12 is illustrated having a generally cylindrical outer surface, the size and shape of the spacer 12 and each of the plurality of segments 20a-20n may be varied by design and by quantity to accommodate the patient anatomy, etiology, and limitations of the delivery system 100 (e.g., the internal dimensions of the catheter lumen).

According to an embodiment, the spacer 12, FIG. 1, may be slidably coupled to the shaft 14. The spacer 12 may include an opening 46 (which may be defined by one or more of the passageways 22a-n) extending from a first end 44 of the spacer 12, through the spacer 12, and to a second end 40. In one such embodiment, the opening 46 may extend generally axially through the spacer 12 and may be sized to slidably receive at least a portion of the shaft 14 therethrough. The shaft 14 may include one or more stops 48, 50. The stops 48, 50 may be sized and/or shaped to control and/or restrict translation of the spacer 12 along the shaft 14 beyond the respective stops 48, 50. In this manner, in the illustrated embodiment, translation of the spacer 12 along the shaft 14 may be restricted to the expanse of the shaft 14 between the stops 48, 50.

One or more of the stops 48, 50 may be integrally formed with the shaft 14. Furthermore, one or more of the stops 48, 50 (such as, but not limited to, stop 50) may be provided as a separate member coupled to and/or formed on the shaft 14. In an embodiment in which one or more of the stops 48, 50 are integrally formed with the shaft 14, the spacer 12 may be slidably coupled to the shaft 14 by pressing the spacer 12 over at least one of the stops 48, 50, which may at least partially elastically deform the opening 46 to permit passage of at least one of the stops 48, 50. Once the one or more of the stops 48, 50 have been pressed through the opening 46, the opening 46 may at least partially elastically recover, thereby resisting passage of the one or more stops 48, 50 back through the opening 46. Various other arrangements may be employed for providing stops on the shaft 14 and/or for controlling and/or limiting translation of the spacer 12 along the shaft 14.

The anchor portion 16 may include a helical member 52 coupled to the shaft 14. As shown, the helical member 52 may be loosely wound such that adjacent turns of the helical member 52 do not contact one another, for example resembling a corkscrew-type configuration. The anchor portion 16 may be engaged with tissue by rotating the anchor portion 16 about the axis of the helical member 52, thereby advancing the anchor portion 16 into tissue. Consistent with such an embodiment, the anchor portion 16 may resist pulling out from the tissue. The anchor portion 16 may be provided as an extension of the shaft 14 wound in a helical configuration. Consistent with related embodiments, the anchor portion 16 may be formed as a separate feature and may be coupled to the shaft 14, e.g., using mechanical fasteners, welding, adhesive, etc.

According to various alternative embodiments, the anchor portion 16 may include various configurations capable of being coupled to and/or otherwise attached to native coronary tissue. For example, the anchor portion 16 may include one or more prongs adapted to pierce coronary tissue and to alone, or in conjunction with other features, resist removal of the anchor portion 16 from tissue. For example, the anchor portion 16 may include a plurality of prongs which may engage native coronary tissue. According to various other embodiments, the anchor portion 16 may include features that may facilitate attachment by suturing. Exemplary features to facilitate suturing may include rings or openings, suture penetrable tabs, etc. Various other anchor portions 16 that may allow attachment or coupling to native coronary tissue may also suitably be employed in connection with the present disclosure.

Turning to FIGS. 2 and 3, the mitral valve implant 10 is shown implanted within a heart 102. The mitral valve implant 10 may be disposed at least partially within the left ventricle 64 of the heart 102. As shown, the anchor portion 16 may be engaged with native coronary tissue within and/or adjacent to the left ventricle 64. The shaft 14, coupled to the anchor portion 16, may extend into the left ventricle 64. The shaft 14 may further extend at least partially within the mitral valve 18, i.e., the shaft 14 may extend at least partially between the cusps or leaflets 19 of the mitral valve 18, and may also extend at least partially into the left atrium 62. The spacer 12 of the mitral valve implant 10 may be positioned at least partially within the left ventricle 64 with the bottom portion 44 within the left ventricle 64 and with the upper portion 40 positioned at least partially within and/or pointed towards the left atrium 62.

FIG. 2 depicts the heart 102 in a condition in which the pressure of blood within the left atrium 62 is at equal to, or higher than, the pressure of blood within the left ventricle 64, e.g., during contraction of the left atrium 62. As shown, when the pressure of blood within the left atrium 62 is greater than or equal to the pressure of blood within the left ventricle 64, blood may flow from the left atrium 62 into the left ventricle 64. The pressure differential and/or the flow of blood from the left atrium 62 to the left ventricle 64 may slidably translate the spacer 12 along the shaft 14 toward the left ventricle 64, in the direction of blood flow between the chambers.

Sliding translation of the spacer 12 along the shaft 14 may at least partially withdraw the spacer 12 from the mitral valve 18 to an open position, as shown. When the spacer 12 is at least partially withdrawn from the mitral valve 18, a passage may be opened between the spacer 12 and the mitral valve 18, allowing blood to flow from the left atrium 62 to the left ventricle 64. Translation of the spacer 12 away from the mitral valve 18 may be controlled and/or limited by the stop 48. In the open position, the stop 48 may maintain the spacer 12 in general proximity to the mitral valve 18 while still permitting sufficient clearance between the mitral valve 18 and the spacer 12 to permit adequate blood flow from the left atrium 62 to the left ventricle 64. Additionally, the flow of blood from left atrium 62 to the left ventricle 64 may cause the mitral valve 18 to flare and/or expand outwardly away from the mitral valve implant 10, permitting blood flow between the implant 10 and the cusps 19 of the mitral valve 19.

As the left ventricle 64 contracts, the pressure of blood in the left ventricle 64 may increase such that the blood pressure in the left ventricle 64 is greater than the blood pressure in the left atrium 62. Additionally, as the pressure of the blood in the left ventricle 64 initially increases above the pressure of the blood in the left atrium 62, blood may begin to flow towards and/or back into the left atrium 62. The pressure differential and/or initial flow of blood from the left ventricle 64 into the left atrium 62 may act against the spacer 12 and may translate the spacer 12 toward the left atrium 104. For example, pressurized blood within the left ventricle 64 may act against the bottom 24 of the spacer 12 inducing sliding translation of the spacer 12 along the shaft 14 toward the left atrium 62.

In the closed position as shown in FIG. 3, the spacer 12 may be translated toward and/or at least partially into the left atrium 62. At least a portion of the spacer 12 may interact with, engage, and/or be positioned adjacent to at least a portion of the mitral valve 18. For example, at least a portion of at least one cusp 19 of the mitral valve 18 may contact at least a portion of the spacer 12. Engagement between the spacer 12 and the mitral valve 18 may restrict and/or prevent the flow of blood from the left ventricle 64 back into the left atrium 62.

In addition to the translation of the spacer 12, the mitral valve 18 may also at least partially close around the spacer 12, thereby also restricting and/or preventing the flow of blood from the left ventricle 64 to the left atrium 62. For example, as mentioned above, at least a portion of one or both of the cusps 19 of the mitral valve 18 may contact at least a portion of the spacer 12. In some embodiments, as the pressure of the blood in the left ventricle 64 increases, the pressure against the bottom 44 of the spacer 12 may increase. The increase in pressure against the bottom 44 of the spacer 12 may, in turn, increase the engagement between the spacer 12 and the mitral valve 18.

Sliding translation of the spacer 12 toward the left atrium 62 may at least partially be controlled and/or limited by the stop 50 coupled to the shaft 14. Additionally, translation of the spacer 12 toward the left atrium 62 may be at least partially limited and/or controlled by engagement between the spacer 12 and the mitral valve 18. One or both of these restrictions on the translation of the spacer 12 may, in some embodiments, prevent the spacer 12 from passing fully into the left atrium 62. Furthermore, the diameter and/or shape of the spacer 12 may limit and/or restrict the movement of the spacer 12 into the left atrium 62.

The preceding embodiment may, therefore, provide a mitral valve implant that is slidably translatable relative to the mitral valve to reduce and/or eliminate regurgitation. Additional embodiments of a mitral valve implant are described in co-pending U.S. patent application Ser. No. 11/258,828, entitled "Heart Valve Implant" filed on Oct. 26, 2005, which is fully incorporated herein by reference. For example, the mitral valve implant may include a generally stationary spacer and may include more than one anchoring portions.

The implant herein has been disclosed above in the context of a mitral valve implant. An implant consistent with the present disclosure may also suitably be employed in other applications, e.g., as an implant associated with one of the other valves of the heart, etc. The present invention should not, therefore, be construed as being limited to use for reducing and/or preventing regurgitation of the mitral valve.

According to one aspect, the present disclosure features a heart valve implant. The heart valve implant may include a shaft extending generally along a longitudinal axis of the heart valve implant. A spacer may comprise a plurality of individual segments each including at least one passageway configured to be disposed about the shaft. The plurality of individual segments may define an outer surface of the spacer configured to interact with at least a portion of at least one cusp of a heart valve to at least partially restrict a flow of blood through the heart valve in a closed position. The heart valve implant may also include at least one anchor configured to be coupled to a first end region of the shaft.

According to another aspect, the present disclosure features a method of introducing a heart valve implant with respect to a heart valve. The method may include providing a heart valve implant comprising a shaft, a spacer including a plurality of individual segments each including at least one passageway configured to be disposed about the shaft, and at least one anchor configured to be coupled to the shaft. The plurality of individual segments may be serially aligned. The aligned plurality of individual segments and the shaft may be percutaneously delivered proximate the heart. The plurality of individual segments may be arranged about shaft to define the spacer wherein the plurality of individual segments define an outer surface of the spacer configured to interact with at least a portion of at least one cusp of the heart valve to at least partially restrict a flow of blood through the heart valve in a closed position. The heart valve implant may also be secured within the heart.

According to yet another aspect, the present disclosure features a heart valve implant system. The heart valve system may include a catheter including a lumen and a heart valve implant. The heart valve implant may comprise a shaft extending generally along a longitudinal axis of the heart valve implant. A spacer may include a plurality of individual segments each having a length and at least one cross-section dimension no larger than an internal cross-section of the lumen. The plurality of individual segments may be configured to be disposed about at least a portion of the shaft to define an outer surface of the spacer configured to interact with at least a portion of at least one cusp of a heart valve to at least partially restrict a flow of blood through the heart valve in a closed position. At least one anchor may be configured to be coupled to a first end region of the shaft.

As mentioned above, the present disclosure is not intended to be limited to a system or method which must satisfy one or more of any stated or implied object or feature of the present disclosure and should not be limited to the preferred, exemplary, or primary embodiment(s) described herein. The foregoing description of a preferred embodiment of the present disclosure has been presented for purposes of illustration and description. It is not intended to be exhaustive or to limit the present disclosure to the precise form disclosed. Obvious modifications or variations are possible in light of the above teachings. The embodiment was chosen and described to provide the best illustration of the principles of the present disclosure and its practical application to thereby enable one of ordinary skill in the art to utilize the present disclosure in various embodiments and with various modifications as is suited to the particular use contemplated. All such modifications and variations are within the scope of the present disclosure as determined by the claims when interpreted in accordance with breadth to which they are fairly, legally and equitably entitled.

What is claimed is:

1. A heart valve implant comprising:
a shaft extending generally along a longitudinal axis of said heart valve implant;
a spacer comprising a plurality of individual segments each including at least one passageway configured to be slidably advanced over said shaft, wherein said plurality of individual segments define an outer surface of said spacer configured to interact with at least a portion of at least one cusp of a heart valve to at least partially restrict a flow of blood through said heart valve in a closed position, wherein at least one of said plurality of individual segments includes a body portion having a generally circular sector cross-section; and
at least one anchor configured to be coupled to a first end region of said shaft, said at least one anchor is selected from the group consisting of a screw, a prong, and a suture.

2. A heart valve implant according to claim 1, wherein each of said plurality of individual segments defines at least a portion of said outer surface of said spacer when said plurality of individual segments are assembled about said shaft.

3. A heart valve implant according to claim 1, wherein at least one of said plurality of individual segments includes a body portion having a generally circular sector cross-section and wherein said at least one passageway is disposed proximate a centerline of said spacer along a longitudinal axis of said at least one segment.

4. A heart valve implant according to claim 1, wherein at least one of said plurality of individual segments includes a body portion having a generally circular sector cross-section and wherein said at least one passageway is disposed through said body portion.

5. A heart valve implant according to claim 1, wherein each of said plurality of individual segments includes a single passageway, wherein each of said passageways are evenly spaced along a longitudinal axis of said plurality of individual segments.

6. A heart valve implant according to claim 1 wherein said plurality of individual segments are configured to move along said longitudinal axis of said shaft.

7. A heart valve implant according to claim 6, wherein at least one of said passageways is configured to rotate about a radial axis of said shaft.

8. A heart valve implant according to claim 6 wherein said at least one of said passageways includes an internal cross-section configured to allow said segment to move along a non-linear portion of said longitudinal axis of said shaft.

9. A heart valve implant according to claim 6, wherein said at least one of said passageways is configured to be substantially non-rotatable about a radial axis of said shaft.

10. A heart valve implant system comprising:
a catheter including a lumen; and
a heart valve implant comprising:
a shaft;
a spacer comprising a plurality of individual segments each having a length and at least one cross-section dimension no larger than an internal cross-section of said lumen, wherein said plurality of individual segments are configured to be slidably advanced over at least a portion of said shaft to define an outer surface of said spacer configured to interact with at least a portion of at least one cusp of a heart valve to at least partially restrict a flow of blood through said heart valve in a closed position, wherein at least one of said plurality of individual segments includes a body portion having a generally circular sector cross-section; and
at least one anchor configured to be coupled to a first end region of said shaft, said at least one anchor is selected from the group consisting of a screw, a prong, and a suture.

11. A heart valve implant system according to claim 10, wherein said plurality of individual segments each include a body portion having a generally circular sector cross-section having a radius which is no larger than an internal diameter of said lumen.

12. A heart valve implant system according to claim 10, wherein said spacer includes at least one cross-sectional dimension which is larger than said internal cross-section of said lumen.

* * * * *